(12) United States Patent
Andersen et al.

(10) Patent No.: US 9,927,554 B2
(45) Date of Patent: Mar. 27, 2018

(54) DIGITAL CORE MODEL CONSTRUCTION

(71) Applicant: Schlumberger Technology Corporation, Sugar Land, TX (US)

(72) Inventors: Mark Andersen, Houston, TX (US); Alexander Nikolaevich Nadeev, Moscow (RU); Igor Andreevich Varfolomeev, Moscow (RU); Ivan Yakimchuk, Moscow (RU); Denis Klemin, Houston, TX (US); Dmitry Anatolievich Koroteev, Moscow (RU); Sergey Sergeevich Safonov, Moscow (RU)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 15/102,269

(22) PCT Filed: Nov. 6, 2014

(86) PCT No.: PCT/US2014/064330
§ 371 (c)(1),
(2) Date: Jun. 6, 2016

(87) PCT Pub. No.: WO2015/084533
PCT Pub. Date: Jun. 11, 2015

(65) Prior Publication Data
US 2017/0032532 A1 Feb. 2, 2017

Related U.S. Application Data

(60) Provisional application No. 61/912,459, filed on Dec. 5, 2013, provisional application No. 61/929,900, filed on Jan. 21, 2014.

(51) Int. Cl.
*G06K 9/34* (2006.01)
*G01V 99/00* (2009.01)
(Continued)

(52) U.S. Cl.
CPC ............ *G01V 99/005* (2013.01); *E21B 49/02* (2013.01); *G01N 23/04* (2013.01); *G01N 33/24* (2013.01);
(Continued)

(58) Field of Classification Search
CPC ...... G01N 23/046; G01N 23/04; G01N 33/24; G01N 2223/616; G01N 2223/649;
(Continued)

(56) References Cited

U.S. PATENT DOCUMENTS 8,081,802 B2 * 12/2011 Dvorkin ............... G01N 23/046
 175/249
8,590,382 B2 * 11/2013 Zaleski, Jr. ........... E21B 43/119
 166/250.01

(Continued)

FOREIGN PATENT DOCUMENTS

WO 2010062839 A1 6/2010
WO 2011002765 A2 1/2011
WO 2012087392 A1 6/2012

OTHER PUBLICATIONS

Digital Image Processing, 3rd Edition, Gonzalez, R.C, Woods, R.E., and Eddins, S.L., Prentice Hall, 2008, Chapter 10 (108 pages).
(Continued)

*Primary Examiner* — Ali Bayat

(57) ABSTRACT

A method and system for analysis of a digital core image obtained from a sample are disclosed. The method includes performing segmentations on the digital core image using multiple approaches to obtain multiple segmented images which are statistically analyzed to select the most suitable approach of the multiple approaches. Thereafter, a digital core model is generated using the segmented image corresponding to the most suitable approach. A simulation test may be performed on the digital core model to obtain a model test result and an oilfield operation may be performed
(Continued)

based on the model test result. The system includes measurement and testing equipment to obtain the digital core image and a computing system including a data repository for storing a digital core image and a digital core model, and a digital core modeling tool. The digital core modeling tool performs the segmentations, statistical analysis, and generates the digital core model.

12 Claims, 16 Drawing Sheets

(51) Int. Cl.
　　*E21B 49/02*　　(2006.01)
　　*G06T 7/11*　　(2017.01)
　　*G06T 7/136*　　(2017.01)
　　*G01N 33/24*　　(2006.01)
　　*G01N 23/04*　　(2018.01)
　　*G06T 7/00*　　(2017.01)
(52) U.S. Cl.
　　CPC .............. *G06T 7/0004* (2013.01); *G06T 7/11* (2017.01); *G06T 7/136* (2017.01); *G06T 2207/10004* (2013.01)
(58) Field of Classification Search
　　CPC ............ G01N 2223/401; G01V 99/005; G06T 2207/10004; G06T 7/11; G06T 7/136; G06T 7/0004; G06K 9/0014; E21B 49/08; E21B 49/02; E21B 49/005; E21B 49/006
　　See application file for complete search history.

(56) References Cited

U.S. PATENT DOCUMENTS

| | | |
|---|---|---|
| 9,507,047 B1 * | 11/2016 | Dvorkin |
| 2011/0288842 A1 | 11/2011 | Gutierrez Ruiz et al. |
| 2012/0029895 A1 | 2/2012 | Xi et al. |
| 2012/0203525 A1 | 8/2012 | Rodriquez Herrera et al. |

OTHER PUBLICATIONS

International Search Report and the Written Opinion issued in the related PCT application PCT/US2014/064330, dated Feb. 16, 2015 (12 pages).

International Preliminary Report on Patentability issued in the related PCT application PCT/US2014/064330, dated Jun. 7, 2016 (8 pages).

Extended Search report issued in the related EP Application 14867199.3, dated Jun. 26, 2017 (10 pages).

Pavel Iassonov et al., Segmentation of X-Ray computed tomography images of porous materials: A Crucial step for characterization and quantitative analysis of pore structures, Water Resources Research, vol. 45, No. 9, Sep. 1, 2009 (12 pages).

Wang W et al., Comparison of image segmentation methods in simulated 2D and 3D microtomographic images of soil aggregates, Geoderma, Elsevier, Amsterdam, NL, vol. 162, No. 3, Jan. 19, 2011, pp. 231-241.

Honglei Zhu et al., A Quantitative evaluation of image segmentation quality, ASPRS 2009 Annual Conference Baltimore, Maryland, Mar. 8, 2009 (4 pages).

* cited by examiner

1. $Q_{FWHH} = 142$ (mask gradient colormap points)
2. $Q_{sigmacontrast} = \sigma_{G_{R_{abs}}}(i_{peak})/\left(\sigma_{G_{R_{abs}}}(0), \sigma_{G_{R_{abs}}}(255)\right) = 14/9$
3. $i_{peak}^{shift} = 153 - 128$
4. $Q_{peakcontrast} = G_{R_{abs}}(i_{peak})/\left(G_{R_{abs}}(0), G_{R_{abs}}(255)\right) = 35/15$ 1. $Q_{FWHH} = 108$ (mask gradient colormap points)
2. $Q_{sigmacontrast} = \sigma_{G_{R_{abs}}}(i_{peak})/\langle\sigma_{G_{R_{abs}}}(0), \sigma_{G_{R_{abs}}}(255)\rangle = 13/8$
3. $i_{peak}^{shift} = 72 - 128$
4. $Q_{peakcontrast} = G_{R_{abs}}(i_{peak})/\langle G_{R_{abs}}(0), G_{R_{abs}}(255)\rangle = 35/14$

DIGITAL CORE MODEL CONSTRUCTION

CROSS-REFERENCES TO RELATED APPLICATIONS

This application claims priority from U.S. Provisional Application 61/912,459, filed Dec. 5, 2013, and U.S. Provisional Application 61/929,900, filed Jan. 21, 2014, both of which are incorporated herein by reference in their entireties.

BACKGROUND

Computer systems provide tools for analyzing various aspects of the world. In order to perform the analysis, virtual models are used. For example, one type of virtual model is a model describing a geological structure (i.e., a physical place). Such model is a virtual representation of the properties of the geological structure (e.g., type of rock, porosity, direction of any formations in the geological structure, and other such properties). The values of the properties may be measured or calculated.

By way of another example, a virtual model may describe mathematical relationships between properties and resulting values. Such a model may be a series of one or more mathematical equations that are used to describe the relationship. In some cases, the mathematical relationship may not be well known or may involve some estimation. In other words, the mathematical model is a heuristic. Thus, to generate such a model, one set of measured values of both the properties and the corresponding resulting values (i.e., both the properties and the resulting values are measured) are used to estimate the relationship.

Combination models may also be used. A combination model describes both the geological structure as well as the mathematical relationship between the values of various properties and the resulting value.

BRIEF SUMMARY OF THE DISCLOSURE

This summary is provided to introduce a selection of concepts that are further described below in the detailed description. This summary is not intended to identify key or essential features of the claimed subject matter, nor is it intended to be used as an aid in limiting the scope of the claimed subject matter.

The present disclosure describes a method and system for analysis of a digital core image obtained from a sample. The method includes performing segmentations on the digital core image using multiple approaches to obtain multiple segmented images which are statistically analyzed to select the most suitable approach of the multiple approaches. Thereafter, a digital core model is generated using the segmented image corresponding to the most suitable approach. A simulation test may be performed on the digital core model to obtain a model test result and an oilfield operation may be performed based on the model test result. The oilfield operation may comprise a survey operation and/or a wellbore operation. The method may also include performing a test on the sample, the sample test matching the simulation test, determining that the sample test result does not match the model test result, updating the segmented image based on the model test result, and determining that the sample test result matches the model test result.

The system includes measurement and testing equipment to obtain the digital core image and a computing system including a data repository for storing a digital core image and a digital core model, and a digital core modeling tool. The digital core modeling tool performs the segmentations and statistical analysis and generates the digital core model. The system may also include a simulation tool to perform a simulation test on the digital core model to obtain a model test result.

BRIEF DESCRIPTION OF THE DRAWINGS

The appended drawings illustrate several embodiments of the disclosed digital core model construction system and method and are not to be considered limiting of its scope.

DETAILED DESCRIPTION

Figure 1:
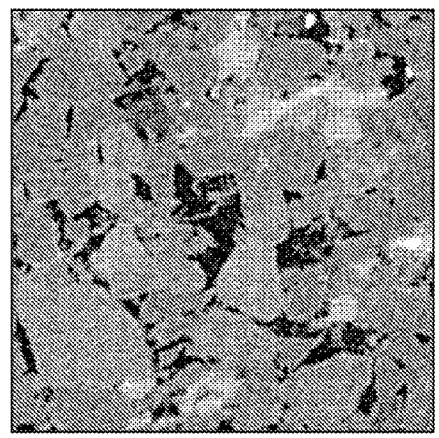
FIG. 1 is an initial two-dimensional (2D) grayscale image of raw geologic data of sandstone which may be used in the disclosed method.

Specific embodiments of the invention will now be described in detail with reference to the accompanying figures. Like elements in the various figures are denoted by like reference numerals for consistency.

In the following detailed description of embodiments of digital core model construction numerous specific details are set forth in order to provide a more thorough understanding of various embodiments. However, it will be apparent to one of ordinary skill in the art that some embodiments may be practiced without these specific details. In other instances, well-known features have not been described in detail to avoid unnecessarily complicating the description.

Glossary

Image

There are a number of techniques for three-dimensional (3D) imaging of a sample: confocal microscopy, ultrasound, SPECT (Single-photon emission computed tomography), MRI (Magnetic resonance imaging), PET (Positron emission tomography), X-ray micro-CT, and others. There are also even more methods producing 2D images such as SEM (Scanning electron microscopy), optical microscopy, fluorescence imaging (such as, LSFM—Laser scanning fluorescence microscopy, X-ray fluorescence analysis), and acoustic/seismic imaging. All these 2D images might be considered as a particular case of a 3D image. One-dimensional (1D) imaging is normally done by profiling devices such as scratching, thermal optical scanner, etc. For readability, below the specification refers to either 1D, 2D, or 3D images as "3D images" or "images".

An image is termed "3D" if it has 3D spatial resolution (see "Coordinate Space and Voxels" section below), although, for example, if each pixel itself is represented with a vector of values, such numerical array might be considered as four-dimensional (4D) (see "Colorspace and Color" section below).

Formally, a multi-dimensional array of numerical values, stored in computer memory, is referred to as a 3D image. This array might be associated with a discrete function $I: \Omega \rightarrow \zeta$, where $\Omega$ is domain (see "Coordinate Space and Voxels" section) of I and $\zeta$ is codomain (see "Colorspace and Color" section) of I.

Coordinate Space and Voxels

The domain [http://en.wikipedia.org/w/index.php?title=Domain_of_a_function&oldid=580242781] of I is referred to as $\Omega$. $\Omega$ is associated with a coordinate space. For example, A=[x, y, z], where x, y, z are spatial coordinates of a voxel on image I that belongs to $\Omega$, which is usually denoted as $A \in \Omega$.

By introducing such a coordinate system other concepts from Euclidean geometry, such as length of vector and spatial gradient are also adopted.

Colorspace and Color

Herein, "colorspace" is defined as codomain [http://en.wikipedia.org/w/index.php?title=Codomain&oldid=582146101] of I. c=I(A), $c \in \zeta$ is usually referenced as "color", although it may represent any physical property (example: X-ray attenuation coefficient). For purposes of readability, and without loss of generality, in examples below, Colorspace is considered to consist of natural numbers in range 0 to 255.

Microporosity

Pores below the resolution of a 3D image are termed "Micro-pores", even if their characteristic scale is different from a few microns. A set of such pores is termed "Microporosity". Substances exhibiting Microporosity are termed "Microporous".

General Description

In general, embodiments provide a method and system for analyzing a core sample. From the core sample, a digital core image of the core sample is obtained. The digital core image may be segmented using a variety of approaches to obtain segmented digital core images. A statistical analysis of each approach is performed using the segmented digital core images to select the most suitable approach. From a digital core image that is segmented using the selected approach a digital core model is generated. The digital core model shows the realistic geometry of the sample and provides information as to the properties of the sample. Using the digital core model, digital core analysis simulations may be performed and field operations may be performed on the digital core model.

When performing the simulations, based on simulation tests using the model and matching tests on the sample, a determination may be made that the segmentation should be updated. By updating the segmentation the model is also updated.

Additionally or alternatively, properties of the model may be determined based on the gradient of the various portions of the digital core image. For example, the volume fraction of micro-pores for a portion of a particular substance may be identified based on the statistical analysis of a gradient map of the portion. Based on the identified properties in the particular portions, the digital core model may be updated.

Figure 15A:
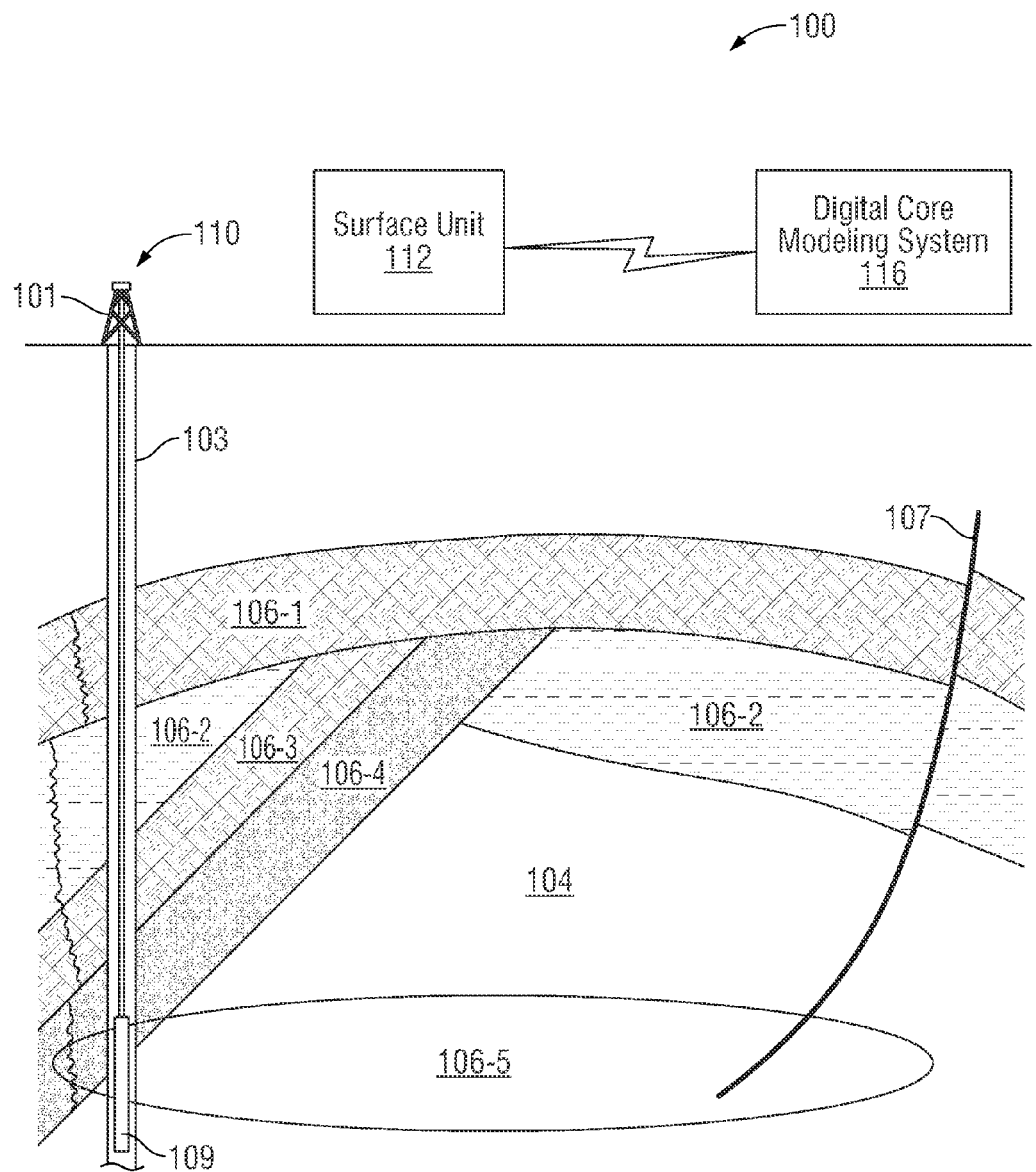
FIGS. 15A, 15B, and 16 show schematic diagrams in accordance with one or more embodiments.

One or more embodiments may be applied to various aspects of oilfield operations. For example, the oilfield operations may occur during the process of exploration, drilling, production, or completion. FIG. 15A depicts a schematic view, partially in cross-section, of an oilfield 100 in which one or more embodiments of user-sourced data issue management may be implemented. In one or more embodiments, one or more of the modules and elements shown in FIG. 15A may be omitted, repeated, and/or substituted. Accordingly, embodiments of user-sourced data issue management should not be considered limited to the specific arrangements of modules shown in FIG. 15A.

As shown in FIG. 15A, the subterranean formation 104 includes several geological structures (106-1 through 106-4). As shown, the formation includes a sandstone layer 106-1, a limestone layer 106-2, a shale layer 106-3, and a sand layer 106-4. A fault line 107 extends through the formation. In one or more embodiments, various survey tools and/or data acquisition tools are adapted to measure the formation and detect the characteristics of the geological structures of the formation. As noted above, the outputs of these various survey tools and/or data acquisition tools, as well as data derived from analyzing the outputs, are considered as part of the historic information.

Further, as shown in FIG. 15A, the wellsite system 110 is associated with a rig 101, a wellbore 103, and other wellsite equipment and is configured to perform wellbore operations, such as logging, drilling, fracturing, production, or other applicable operations. Generally, survey operations and wellbore operations are referred to as oilfield operations of the oilfield 100. These oilfield operations may be performed as directed by the surface unit 112.

In one or more embodiments, the surface unit 112 is operatively coupled to a digital core modeling system 116 and/or a wellsite system 110. In particular, the surface unit 112 is configured to communicate with the digital core modeling system 116 and/or the wellsite system 110 to send commands to the digital core modeling system 116 and/or the wellsite system 110 and to receive data therefrom. For example, the wellsite system 110 may be adapted for measuring downhole properties using logging-while-drilling (LWD) tools and for obtaining core samples. In one or more embodiments, the surface unit 112 may be located at the wellsite system 110 and/or remote locations. The surface unit 112 may be provided with computer facilities for receiving, storing, processing, and/or analyzing data from the digital core modeling system 116, the wellsite system 110, or other part of the oilfield 100. The surface unit 112 may also be provided with functionally for actuating mechanisms at the oilfield 100. The surface unit 112 may then send command signals to the oilfield 100 in response to data received, for example to control and/or optimize various oilfield operations described above.

In one or more embodiments, the data received by the surface unit 112 represents characteristics of the subterranean formation 104 and may include seismic data and/or information related to porosity, saturation, permeability, natural fractures, stress magnitude and orientations, elastic properties, etc. during a drilling, fracturing, logging, or production operation of the wellbore 103 at the wellsite system 110.

In one or more embodiments, the surface unit 112 is communicatively coupled to the digital core modeling system 116. Generally, the digital core modeling system 116 is configured to analyze, model, control, optimize, or perform other management tasks of the aforementioned oilfield operations based on the data provided from the surface unit 112. Although the surface unit 112 is shown as separate from the digital core modeling system 116 in FIG. 15A, in other examples, the surface unit 112 and the digital core modeling system 116 may also be combined.

Figure 15B:
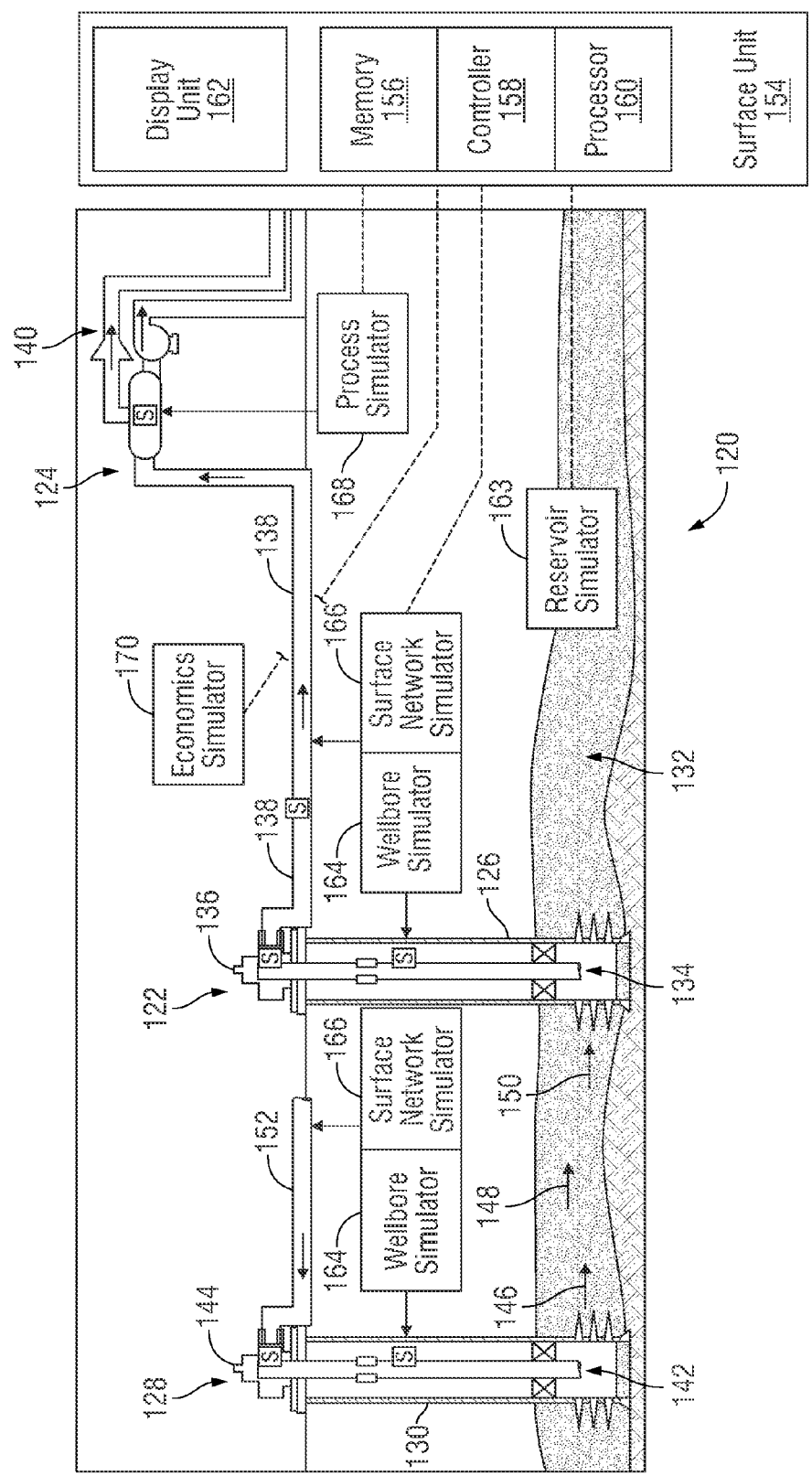

FIG. 15B shows a schematic view of a portion of the oilfield 120 of FIG. 15A, depicting a producing wellsite 122 and surface network 124 in detail. The wellsite 122 of FIG. 15B includes a wellbore 126 extending into the earth therebelow. In addition, FIG. 15B shows an injection wellsite 128 having an injection wellbore 130. As shown, the wellbores 126 and 130 have already been drilled, completed, and prepared for production from reservoir 132.

Wellbore production equipment 134 extends from a wellhead 136 of wellsite 122 and to the reservoir 132 to draw fluid to the surface. The wellsite 122 is operatively connected to the surface network 124 via a transport line 138. Fluid flows from the reservoir 132, through the wellbore 126, and into the surface network 124. The fluid then flows from the surface network 124 to the process facilities 140.

As described above, fluid may be injected through an injection wellbore, such as the wellbore 130 to gain additional amounts of hydrocarbon production. Fluid may be injected to sweep hydrocarbons to producing wells and/or to maintain reservoir pressure by balancing extracted hydrocarbons with injected fluid. The wellbore 130 may be a new well drilled specifically to serve as an injection wellbore, or an already existing well that is no longer producing hydrocarbons economically. As shown in FIG. 15B, wellbore injection equipment 142 extends from a wellhead 144 of injection wellsite 128 to inject fluid (e.g., shown as 146 and 148 in FIG. 15B) in or around the periphery of the reservoir 132 to push hydrocarbons (e.g., shown as 150 in FIG. 15B) toward a producing wellbore, such as the wellbore 126. The injection wellsite 128 is operatively connected to an injection transport line 152, which provides the injection fluid to the injection wellsite 128 through the wellhead 144 and down through the well injection equipment 142.

As further shown in FIG. 15B, sensors S are located about the oilfield 120 to monitor various parameters during oilfield operations. The sensors S may measure, for example, pressure, temperature, flow rate, composition, and other parameters of the reservoir, wellbore, surface network, process facilities, and/or other portions of the oilfield operation. The sensors S are operatively connected to a surface unit 154 for collecting data therefrom. The surface unit may be, for example, similar to the surface unit 112 of FIG. 15A.

One or more surface units 154 may be located at the oilfield 120, or linked remotely thereto. The surface unit 154 may be a single unit, or a complex network of units used to perform the modeling, planning, and/or management functions throughout the oilfield 120. The surface unit 154 may be a manual or automatic system. The surface unit 154 may be operated and/or adjusted by a user. The surface unit 154 is adapted to receive and store data. The surface unit 154 may also be equipped to communicate with various oilfield equipment. The surface unit 154 may then send command signals to the oilfield in response to data received or modeling performed.

As shown in FIG. 15B, the surface unit 154 has computer facilities, such as memory 156, controller 158, processor 160, and display unit 162, for managing the data. The data is collected in memory 156, and processed by the processor 160 for analysis. Data may be collected from the oilfield sensors S and/or by other sources. For example, oilfield data may be supplemented by historical data collected from other operations, or user inputs.

The analyzed data (e.g., based on modeling performed) may then be used to make decisions. A transceiver may be provided to allow communications between the surface unit 154 and the oilfield 120. The controller 158 may be used to actuate mechanisms at the oilfield 120 via the transceiver and based on these decisions. In this manner, the oilfield 120 may be selectively adjusted based on the data collected. These adjustments may be made automatically based on computer protocol and/or manually by an operator. In some cases, well plans are adjusted to select optimum operating conditions or to avoid problems.

To facilitate the processing and analysis of data, simulators may be used to process the data for modeling various aspects of the oilfield operation. Specific simulators are often used in connection with specific oilfield operations, such as reservoir or wellbore simulation. Data fed into the simulator(s) may be historical data, real time data, or combinations thereof. Simulation through one or more of the simulators may be repeated or adjusted based on the data received.

As shown, the oilfield operation is provided with wellsite and non-wellsite simulators. The wellsite simulators may include a reservoir simulator 163, a wellbore simulator 164, and a surface network simulator 166. The reservoir simulator 163 solves for hydrocarbon flow through the reservoir rock and into the wellbores. The wellbore simulator 164 and surface network simulator 166 solves for hydrocarbon flow through the wellbore and the surface network 124 of pipelines. As shown, some of the simulators may be separate or combined, depending on the available systems.

The non-wellsite simulators may include process 168 and economics 170 simulators. The processing unit has a process simulator 168. The process simulator 168 models the processing plant (e.g., the process facilities 140) where the hydrocarbon(s) is/are separated into its constituent components (e.g., methane, ethane, propane, etc.) and prepared for sale. The oilfield 120 is provided with an economics simulator 170. The economics simulator 170 models the costs of part or the entire oilfield 120 throughout a portion or the entire duration of the oilfield operation. Various combinations of these and other oilfield simulators may be provided.

Figure 16:
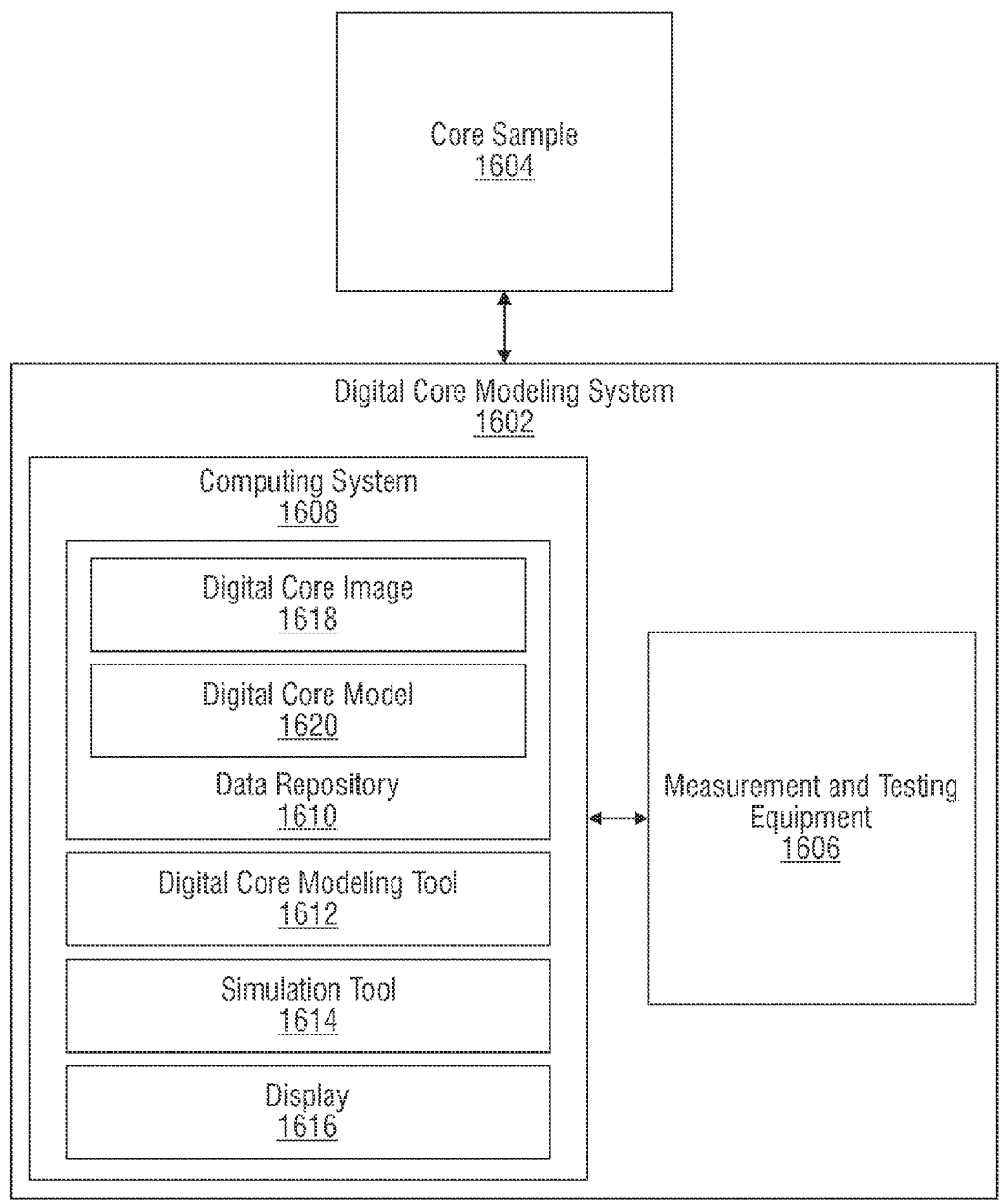

FIG. 16 shows a schematic diagram of the digital core modeling system 1602 in accordance with one or more embodiments. As discussed above, the digital core modeling system 1602 may include at least a portion of the surface unit shown and described in relation to FIG. 15A and FIG. 15B.

As shown in FIG. 16, the digital core modeling system 1602 interfaces with a core sample 1604. A core sample 1604 is a three-dimensional (3D) medium representing a geological region. For example, the geological region may correspond to a portion of an oilfield. In particular, a core sample refers to a physical sample obtained from the geological region. For example, the core sample 1604 may be obtained by drilling into the portion of the oilfield with a core drill to extract the core sample 1604.

The digital core modeling system 1602 includes functionality to generate a digital core model 1620 of the core sample 1604 and use the digital core model 1620 to perform various simulations. The digital core modeling system 1602 may also include functionality to perform various tests on the core sample 1604 in order to identify various properties of the core sample 1604 and perform simulations on the core sample 1604. The digital core modeling system 1602 may include hardware, software, firmware, or a combination thereof. The digital core modeling system 1602 includes measurement and testing equipment 1606 and a computing system 1608.

In one or more embodiments, the measurement and testing equipment corresponds to various pieces of equipment for performing measurements and conducting tests on the core sample 1604. For example, the measurement and testing equipment 1604 may include equipment for performing computed tomography (CT) scanning, scanning electron microscopy, focused ion beam scanning electron microscopy, confocal microscopy, routine and special core analysis equipment.

At least a portion of measurement and testing equipment 1606 may include functionality to interface directly with the computing system 1608. Specifically, the measurement and testing equipment 1606 may include functionality to provide data from the measurements and tests to the computing system 1608 and to receive instructions and parameters for tests from the computing system 1608.

The computing system 1608 may include hardware, software, firmware, or a combination thereof. Various components of the computing system 1608 are described below with reference to FIG. 20.

Figure 20:
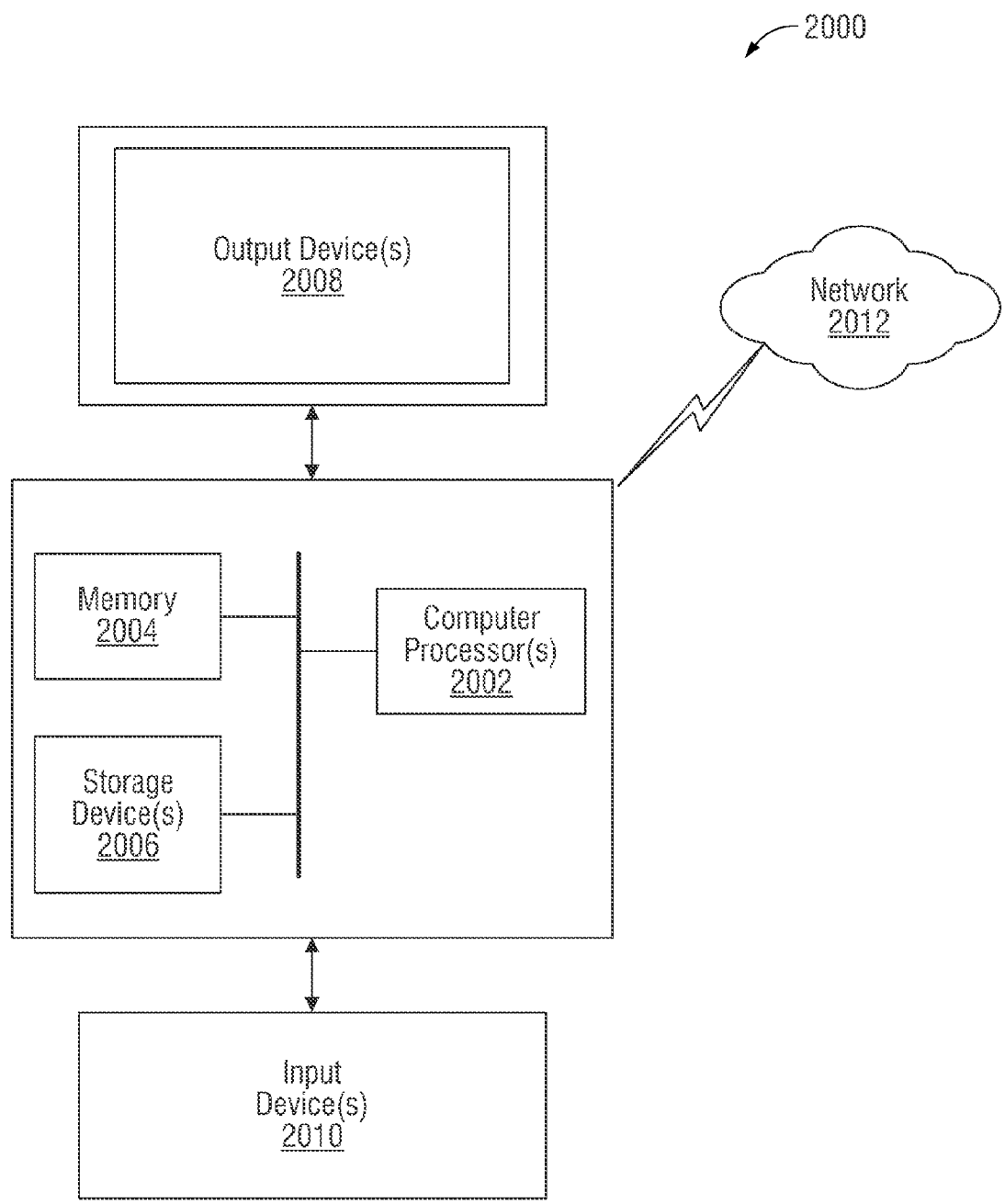
FIG. 20 shows a computing system in accordance with one or more embodiments.

As shown in FIG. 20, the computing system 2000 may be of virtually any type regardless of the platform being used. For example, the computing system 2000 may be one or more mobile devices (e.g., laptop computer, smart phone, personal digital assistant, tablet computer, or other mobile device), desktop computers, servers, blades in a server chassis, or any other type of computing device or devices that includes at least the minimum processing power, memory, and input and output device(s) to perform one or more embodiments of the invention. For example, as shown in FIG. 20, the computing system 2000 may include one or more computer processor(s) 2002, associated memory 2004 (e.g., random access memory (RAM), cache memory, flash memory, etc.), one or more storage device(s) 2006 (e.g., a hard disk, an optical drive such as a compact disk (CD) drive or digital versatile disk (DVD) drive, a flash memory stick, etc.), and numerous other elements and functionalities. The computer processor(s) 2002 may be an integrated circuit for processing instructions. For example, the computer processor(s) may be one or more cores, or micro-cores of a processor. The computing system 2000 may also include one or more input device(s) 2010, such as a touchscreen, keyboard, mouse, microphone, touchpad, electronic pen, or any other type of input device. Further, the computing system 2000 may include one or more output device(s) 2008, such as a screen (e.g., a liquid crystal display (LCD), a plasma display, cathode ray tube (CRT) monitor, e-ink display, projector, or other display device), a printer, external storage, or any other output device. One or more of the output device(s) may be the same or different from the input device(s). The computing system 2000 may be connected to a network 2012 (e.g., a local area network (LAN), a wide area network (WAN) such as the Internet, mobile network, or any other type of network) via a network interface connection. The input and output device(s) may be locally or remotely (e.g., via the network 2012) connected to the computer processor(s) 2002, memory 2004, and storage device(s) 2006. Many different types of computing systems exist, and the aforementioned input and output device(s) may take other forms.

Software instructions in the form of computer readable program code to perform one or more embodiments may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that when executed by a processor(s), is configured to perform one or more embodiments of digital core model construction.

Further, one or more elements of the aforementioned computing system (2000) may be located at a remote location and connected to the other elements over a network (2012). Further, embodiments may be implemented on a distributed system having multiple nodes, where each portion of an embodiment may be located on a different node within the distributed system. In one or more embodiments, the node corresponds to a distinct computing device. Alternatively, the node may correspond to a computer processor with associated physical memory or to a computer processor or micro-core of a computer processor with shared memory and/or resources.

Returning to FIG. 16, the computing system (1608) includes a data repository (1610), a digital core modeling tool (1612), a simulation tool (1614), and display (1616). Each of these components is described below.

In one or more embodiments, the data repository (1610) is any type of storage unit and/or device (e.g., a file system, database, collection of tables, or any other storage mechanism) for storing data. Further, the data repository (1610) may include multiple different storage units and/or devices. The multiple different storage units and/or devices may or may not be of the same type or located at the same physical site.

The data repository (1610) includes functionality to store a digital core image (1618) and a digital core model (1620). The digital core image (1618) of the core sample (1604) is represented in accordance with the definition in the "Image" section above. Specifically, the digital core image is an image of each portion of the core sample (1604) including pores and solid surfaces. Thus, the digital core image (1618) may reflect pores and rock boundaries of the core sample for each layer of the core sample.

In one or more embodiments, the pores, rock boundaries, and other properties of the digital core image may be reflected in the particular color or intensity of each voxel. In other words, the digital core image does not explicitly include identifiers of the various properties, but rather the digital core image may be analyzed to identify the various properties of each portion or voxel of the digital core image.

The digital core model (1620) is a model of the core sample (1604). Specifically, the digital core model (1620) explicitly includes the properties of the core sample (1604). Specifically, whereas the digital core image (1618) may show the physical structure of the core sample (1604), the digital core model (1620) may include the lithology of the core sample (1604). For example, the lithographic properties of the core sample (1604) may include pore size distribution, rock type, tortuosity measurements, statistical results generated from the properties, and other information. The digital core model (1620) may include various mathematical relationships between the properties and the resulting values. Similar to the digital core image (1618), the digital core model (1620) may also include voxels where each voxel includes information about certain properties. Other techniques besides voxels may be used for the core sample (1604) without departing from the scope of one or more embodiments.

Continuing with FIG. 16, the digital core modeling tool (1612) includes functionality to obtain a digital core image (1618) from the measurement and testing equipment (1606) and generate a digital core model (1620). Generating the digital core model (1620) is discussed below and in FIGS. 17-18 in accordance with one or more embodiments.

The simulation tool (1614) includes functionality to perform simulations on the digital core model (1620). Specifically, the simulations simulate various scenarios on the core sample (1604). The purpose of the simulations are to identify additional properties of the core sample (1604), to validate the digital core model (1620), to identify how the core sample (1604) may be affected by the example scenarios, to extrapolate the simulation results to identify how the field (e.g., oilfield or other geographic region) may be affected by performing the example scenario in the field, or to perform another task or combination thereof. The simulation tool (1614) may include various input parameters describing an example scenario and generate a simulation result for the example scenario.

In one or more embodiments, the display (1616) is a hardware component that includes functionality to display at least a portion of the digital core image (1618), the digital core model (1620), and simulation results. Further, the display (1616) may include functionality to display a user interface for a user to interact with the various components of the computing system (1608).

While FIGS. 15A, 15B, and 16 show a configuration of components, other configurations may be used without departing from the scope of embodiments. For example, various components may be combined to create a single component. As another example, the functionality performed by a single component may be performed by two or more components.

Figure 17:
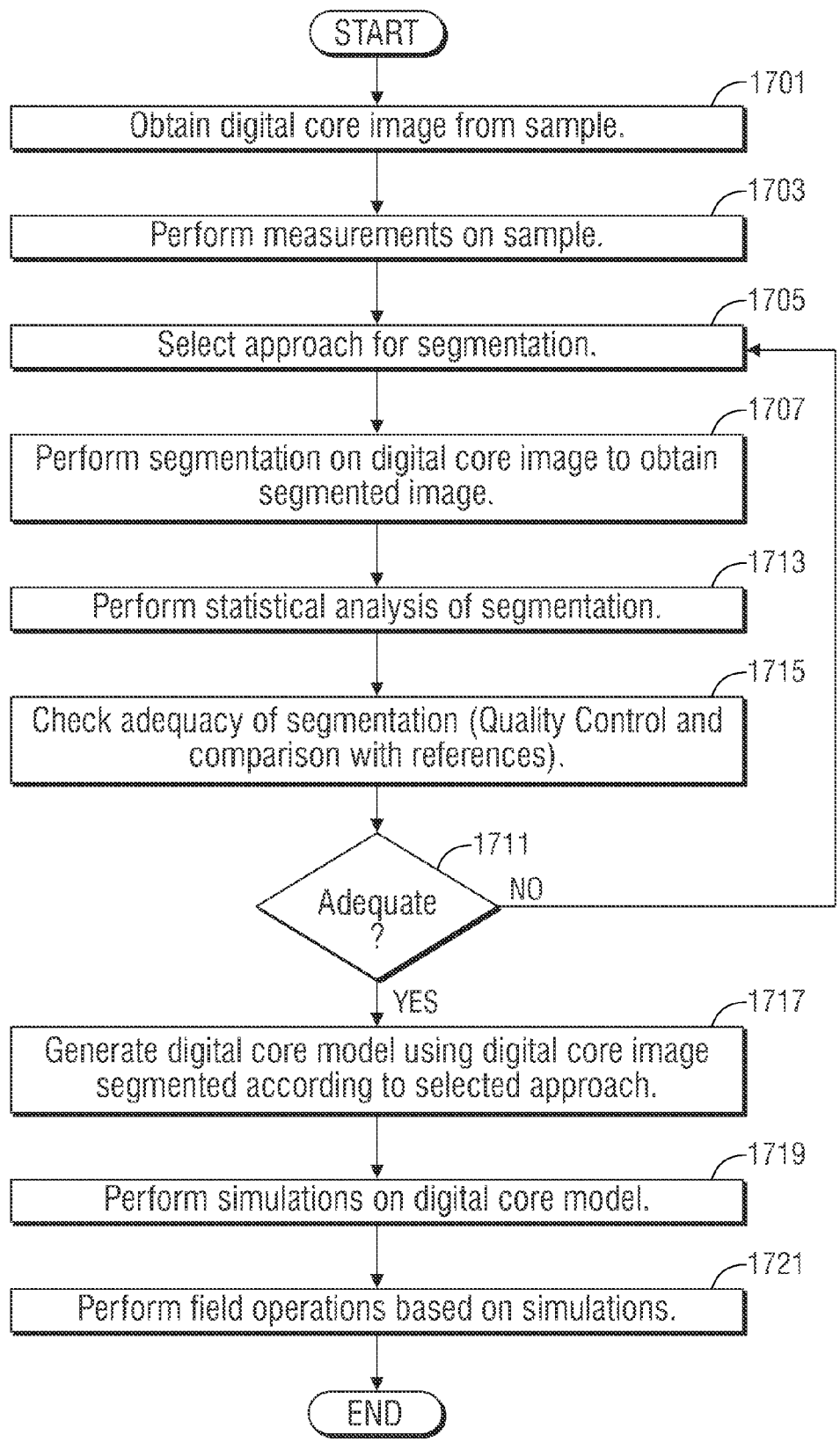
FIGS. 17-19 show flowcharts in accordance with one or more embodiments.
Figure 18:
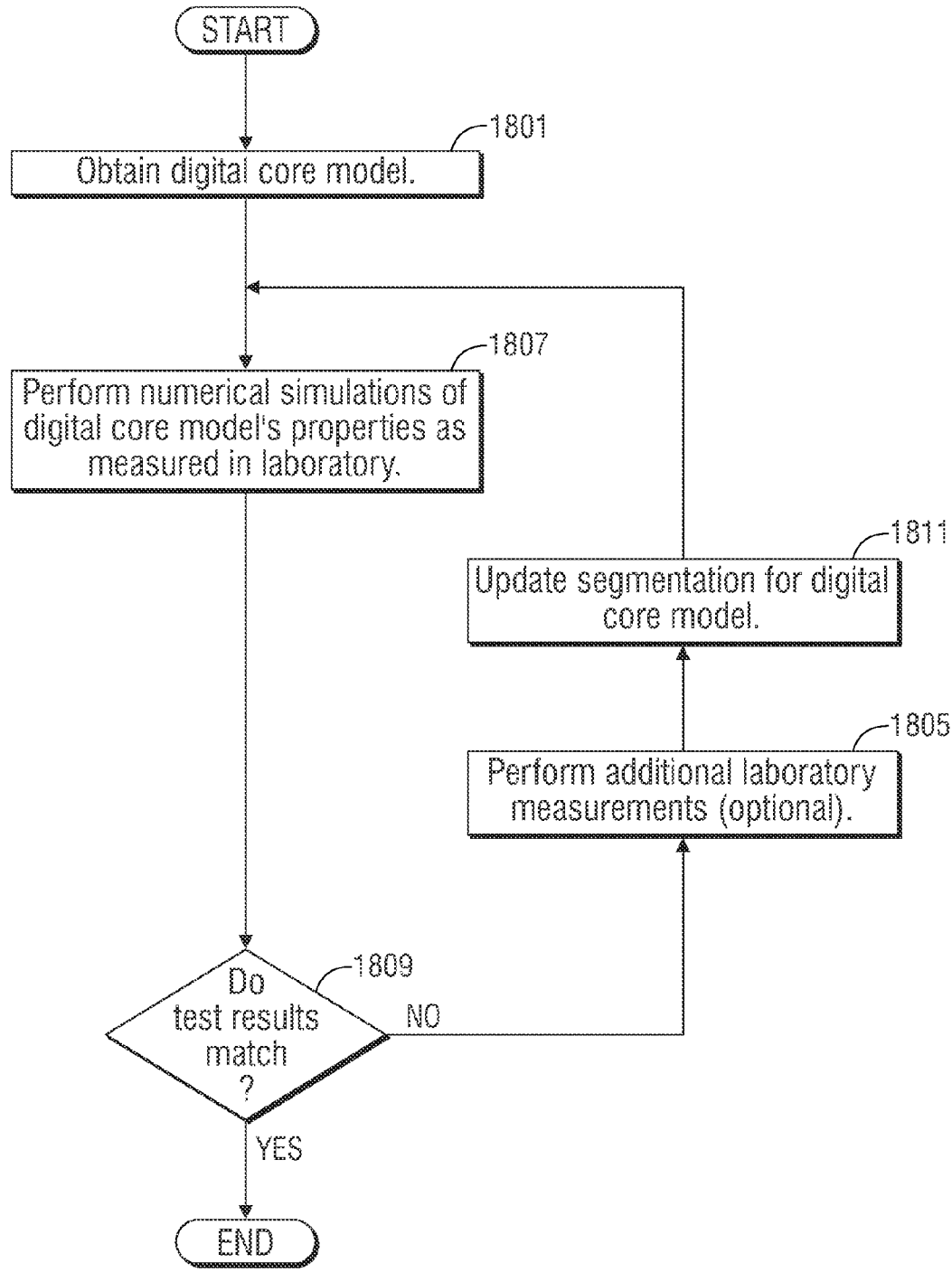
Figure 19:
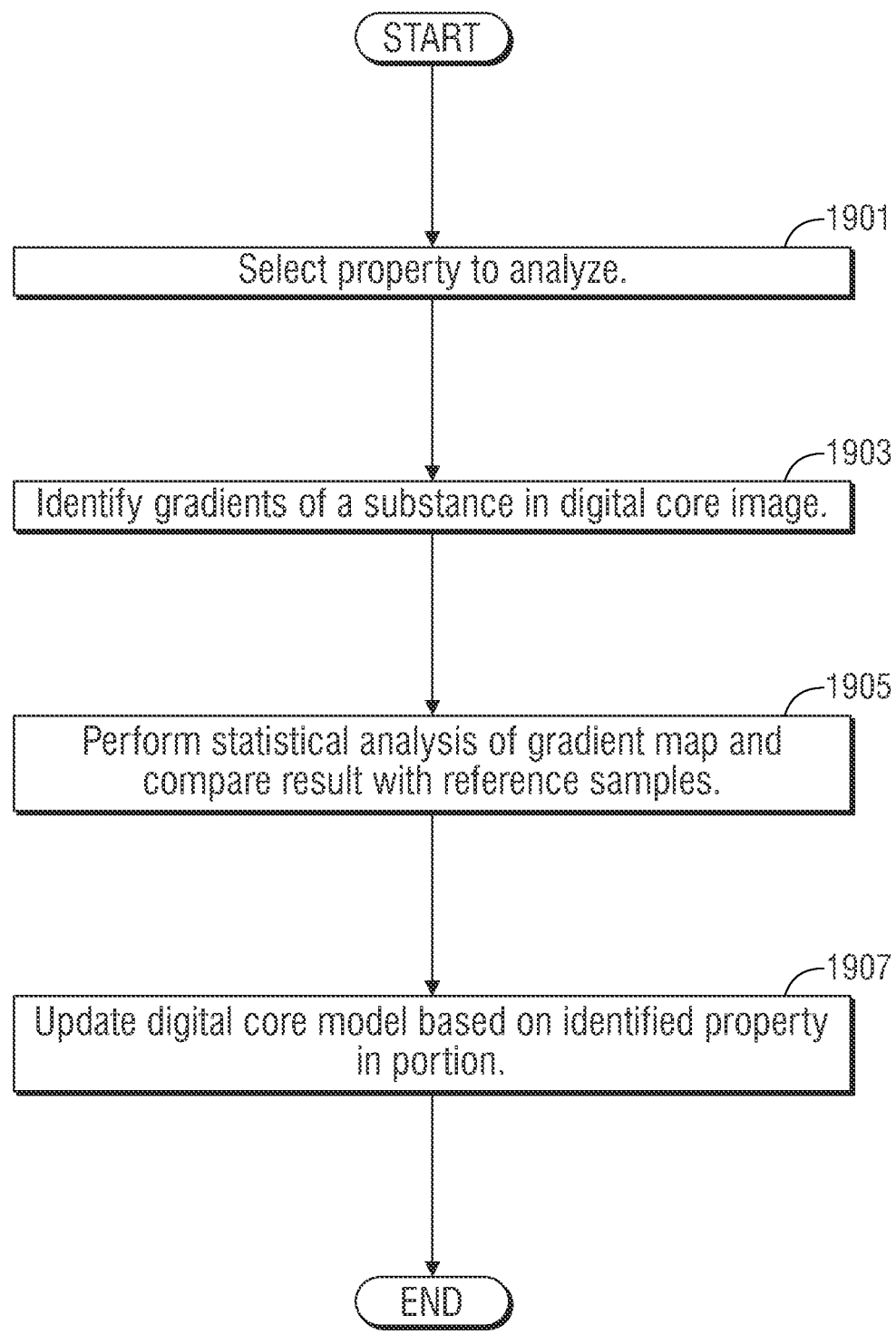

FIGS. 17-19 show flowcharts in accordance with one or more embodiments. While the various blocks in these flowcharts are presented and described sequentially, one of ordinary skill will appreciate that some or all of the blocks may be executed in different orders, may be combined or omitted, and some or all of the blocks may be executed in parallel. Furthermore, the blocks may be performed actively or passively. For example, some blocks may be performed using polling or be interrupt driven in accordance with one or more embodiments. By way of example, determination blocks may not require a processor to process an instruction unless an interrupt is received to signify that a condition exists in accordance with one or more embodiments of the invention. As another example, determination blocks may be performed by performing a test, such as checking a data value to test whether the value is consistent with the tested condition in accordance with one or more embodiments of the invention.

Overall Workflow

Turning to FIG. 17, FIG. 17 shows a flowchart for performing analysis using a digital core sample. In block 1701, a digital core image is obtained from a sample in accordance with one or more embodiments. In one or more embodiments, a core sample of a rock or other porous material is evaluated using multi-scale imaging to obtain the core sample image. Different techniques may be performed to obtain the core sample image, such as computed tomography, scanning electron microscopy, focused ion beam scanning electron microscopy, confocal microscopy, or other technique, or combination thereof that results in a 2D or 3D digital representation of the core sample.

In block 1703, measurements are performed on the sample in accordance with one or more embodiments. Measurements in one or more laboratory tests on the same or a representative similar rock or other porous medium provide one or more physical properties of the material. These laboratory test measurements may include routine core analysis, special core analysis, or other analysis or combination thereof. Data from the measurements and tests may include a variety of experimental parameters. Examples of the data include porosity, mineralogy, wettability, electrical conductivity, chemical reactivity, fluid pressures, boundary or confining pressures, differential pressures, temperatures, flow rates of various fluid phases, fluid compositions, fluid rheology, fluid phase conditions and behavior, mobile solid composition and concentration, interfacial tensions, surface tensions and their distribution within the sample for each particular fluid phase, and changes in any of these properties or conditions during the test. The data also may include details of the equipment used to perform the laboratory test. Further, additional or alternative data may be included without departing from the scope of some embodiments.

The additional tests and measurements may be performed on the core sample in order to obtain information about the core sample. Such information may include what types of substances are identified in the core sample without identifying the specific location of the substances in the core sample or without identifying all locations in the core sample in which the types of substances are identified.

In block 1705, an approach for segmentation is selected in accordance with one or more embodiments.

In particular, as discussed above, the digital core image may have a large number of different colors and/or intensities, such that the same substance in various positions in the digital core image has a variety of colors and/or intensities. One or more embodiments of the invention use thresholding to transform the large number of different colors and/or intensities to a countable number of colors and/or intensities. By way of an example, a large number of colors and/or intensities may be 256 or greater number of possible colors and/or intensities whereas a countable number of colors and/or intensities may be 128 or less possible number of colors and/or intensities. By way of an example, as discussed above, if the voxel is represented by 8 bits in the digital core image, than the voxel may take any of 256 colors and/or intensities whereas the segmentation allows a voxel to have any of 5 colors and/or intensities. Although the voxel may have a variety of colors and/or intensities, not all colors and/or intensities may be represented in the digital core image or the segmented image.

In order to perform the reduction from the large number to the countable number, segmentation is performed. Segmentation is a well-known technique described in, for example, *Digital Image Processing*, 3$^{rd}$ Edition, Gonzalez, R. C, Woods, R. E., and Eddins, S. L., Prentice Hall, 2008, Chapter 10, incorporated herein by reference. In one or more embodiments, the approach for segmentation defines where one or more thresholds are placed in order to differentiate various substances. Specifically, segmentation may be performed based on global thresholding. Thus, during analysis of grayscale histogram or color based histogram, the thresholding level is selected to distinguish one phase from another. Such thresholding level may be selected manually or automatically. The technique for selecting the thresholding level and/or the position of the thresholds can be applied. By way of an example, the thresholding level may be directly in between two peaks of the histogram, somewhere in between the two peaks of the histogram, or in the middle of a single large peak. If more than two peaks exist indicating the presence of multiple substances, multiple phases may be defined by applying more than one threshold. The different sectors of the histogram as defined by the number of thresholds define the number of phases in accordance with one or more embodiments.

Choice of segmentation algorithm and its parameters can also be based on:
a. lithological type of the sample,
b. results of laboratory measurements (block 1703),
c. adequacy (as estimated by block 1715) of previous segmentations of this or similar (similar from the view of (a) and (b)) samples.

For example, a specific segmentation method might be chosen based on knowledge that the sample is a certain sandstone, with permeability of 9 milliDarcy, electrical formation factor of 1.8, and porosity of 28%, and not featuring any microporosity, and additional knowledge that previously a similar model of the same sandstone formation was created using a specific algorithm of determining peak thresholds and simple binarization. All this information could be stored inside the disclosed device in a specially configured database. Also, the choice of closest previous match can be readily automated.

In block 1707, segmentation is performed on the digital core image or its representative part to obtain a segmented image in accordance with one or more embodiments. Image segmentation is a type of clusterization to different phases (number of phases is usually greater than or equal to two) with a defined range of grayscale or color level. After segmentation, each phase has only one color instead of a range of colors (e.g., range of gray colors). Segmentation is also a type of image simplification.

In one or more embodiments, the following methods may be used to perform block 1707. A first method is to segment into all phases simultaneously from the initial grayscale image. A second method is to binarize into two phases (e.g., phase of interest and remainder of the material) at a time. The second method focuses on identifying each substance sequentially and then combining the information to create the segmented image.

In block 1713, a statistical analysis is performed for each approach of the segmentation in accordance with one or more embodiments. In one or more embodiments, the statistical analysis is based on gradient and distance map calculation. An example of such statistical analysis is presented below with reference to FIGS. 1-14. Other statistical analysis may be performed without departing from the scope of some embodiments.

In block 1715, the adequacy of the selected segmentation approach is estimated based on the results of statistical analysis in accordance with one or more embodiments. Specifically, one or more embodiments select the approach that best matches the core sample according to the analysis. In particular, an approach best matches the core sample when the segmentation accurately reflects the locations of different substances in the core sample. An example set of factors for selecting an approach is presented below with reference to FIGS. 1-14. Another criterion is correspondence of statistical analysis results (e.g. Edge Profile) with reference data, if any are known a priori for the type of sample being studied.

In block 1711, a determination is made whether to apply another approach in accordance with one or more embodiments. Specifically, multiple different thresholding approaches may be identified and selected in turn.

In block 1717, a digital core model is generated using the digital core image that is segmented according to the selected approach in accordance with one or more embodiments. In one or more embodiments, the segmented digital core image (i.e., digital core image that is segmented according to the selected approach) is used to identify the location of the various substances in the core sample. In other words, the segmentation defines which substance corresponds to each voxel and maps the substance information to the voxel. By identifying which substance corresponds to each voxel, information about the substance may be explicitly stored, directly or indirectly, with the voxel in the digital core model. Thus, whereas the substance information for the digital core image is only with reference to a large number of colors and/or intensities and is not well defined for any particular voxel, the substance information for the digital core model is well defined for each voxel. The quality check assists in ensuring the accuracy of the substance information to the voxel. As part of creating the digital core model, other properties from other analysis and tests with the core sample and digital core image may also be stored and associated with the various voxels. Although the above describes the digital core model as having voxels, the voxels may be mapped to a different mechanism that identifies the location of properties without departing from the scope of one or more embodiments. The process, shown in FIG. 19 may be used to determine and incorporate several additional physical properties of the sample to the digital core model. Further, as in FIG. 18, the results of simulations and tests on the core sample may be used to validate the digital core model.

In block 1719, simulations are performed on the digital core model in accordance with one or more embodiments. In one or more embodiments, the simulations have, as input parameters, example scenarios to apply to the digital core model. The simulations may simulate how the core sample and, subsequently, the field react to the example scenarios. For example, the simulations may simulate how various fluids flow through the core sample which may give an indication of how the various fluids would flow through the spatial region from which the core sample was obtained.

In block 1721, field operations are performed based on the simulations in accordance with one or more embodiments. Specifically, the digital core modeling system and/or user may transmit information and manage the physical equipment at the field according to the simulations. For example, the scenario that results in the best possible predicted output may be performed in the field. For an oilfield, the field operations and the example scenarios that may be applied may include scenarios that define the amount and type of injection fluid, drilling speed, drilling location, and/or other operations of the oilfield.

Validating Properties of Digital Core Model

FIG. 18 shows a flowchart for performing a quality check on the digital core model based on simulation tests.

In block 1801, a digital core model is obtained from a digital core sample. Obtaining the digital core model may be performed in the same or similar manner as that discussed above with reference to FIG. 17.

In block 1807, tests are performed on the digital core model to obtain model test results in accordance with one or more embodiments. The tests that are performed may include performing the simulations discussed above with respect to block 1719. For the purposes of quality control, the tests that are performed and used in the quality control match are identical or similar to the tests and measurements performed on the core sample.

In block 1809, a determination is made whether the test results match in accordance with one or more embodiments. Specifically, a determination is made whether the model test results accurately, within an error threshold, represent the sample test results. If the test results do match, then the digital core model may be deemed to be accurate.

If the test results do not match, in block 1805 additional laboratory measurements may be performed on the sample to obtain sample test results in accordance with one or more embodiments. In particular, one or more example scenarios may be performed on the core sample. Further, various measurements of the core sample with and without the example scenarios may be obtained using the testing and measurement equipment. The measurement and testing equipment may provide the information directly or indirectly to the digital core model computing system.

Next, in block 1811, the segmentation for the digital core model is updated in accordance with one or more embodiments. In particular, the digital core model is updated. One mechanism or parameter that may be used to update the digital core model is to select different parameters (e.g. voxel size, or substance electrical conductivity) used for model creation (i.e. go back to block 1717), or to select different segmentation method parameters (i.e. go back to block 1705). Other parameters and/or properties may be adjusted in one or more embodiments of the invention. After updating the digital core model, the method may repeat starting with block 1807 to perform tests on the updated digital core model.

Correlating Physical Properties of the Core Sample and Edge Profile

Some physical properties of porous samples (those largely depending on surface of grains), such as
 a. surface-specific microporosity (e.g. pores, with characteristic size below the resolution of the imaging device, located near the surface of grain, which is common for some types of rocks);
 b. wettability (which largely depends on thin layers of various substances near the surface of the grain); and
 c. electrical properties (which largely depend on wettability);
can be correlated with the Edge Profile, which is more sensitive to low-contrast, thin and below-resolution features than algorithms based on explicitly removing such features through segmentation, because of the larger statistics available—all surfaces of the specific mineral are considered at once. However, due to the nature of the statistical analysis being used, each substance-to-substance interface is studied separately, so, physical properties may be not only correlated to the whole sample, but also to a specific mineral within it.

FIG. 19 shows a flowchart for updating a digital core model in accordance with one or more embodiments. In block 1901, a physical property to analyze is selected in accordance with one or more embodiments. Various properties may be selected. For example, the physical property may be microporosity (e.g., the amount of micropores in a substance), electrical conductivity, wettability, or another physical property. Different properties may be correlated with different Edge Profiles, calculated independently. Moreover, a single physical property may be correlated with a set of Edge Profiles.

In block 1903, gradients of a substance in a digital core image are identified in accordance with one or more embodiments. In block 1905, for each portion of the substance, the physical property is identified based on known correlation of this property and results of statistical analysis of the gradient map in accordance with one or more embodiments. In other words, intensity information or color information of a particular portion of substance may be used to identify a measure, such as amount or quantity, of the physical property in the portion. To determine a mapping between statistical properties of gradient maps and values of the physical property, one may use a set of reference data, which may be stored in a specially configured database.

For example, consider a study of a sample featuring surface-specific microporosity. Being provided a priori with N different samples of the same lithological type e.g.:
 a. amount of surface-specific microporosity in them (e.g. in cubic microns per square micron of grain surface), and
 b. their Edge Profiles,
 one may compare Edge Profile of $(N+1)^{th}$ sample to those of first N samples (e.g. using L2-norm [http://en.wikipedia.org/w/index.php?title=Lp_space&oldid=624906026]). Thus, by finding a close match, one finds the estimated amount of microporosity in the $(N+1)^{th}$ sample.

In block 1907 the digital core model is updated based on the identified physical property in the portion in accordance with one or more embodiments. Specifically, the digital core model is updated with the measure of the physical property in the particular portion.

Statistical Analysis

FIGS. 1-14 show examples in accordance with one or more embodiments. The following is an example and the examples shown in the FIGS. 1-14 are for explanatory purposes only and not intended to limit the scope of some embodiments. For the purposes of the example, the digital core image is a grayscale image. However, a multi-channel image may be used without departing from the scope of one or more embodiments.

An algorithm is aimed to analyze, for example, 3D tomographic data segmentation quality. The algorithm may include functionality to estimate several properties of raw grayscale images and segmented data, such as raw image gradient length, segmentation threshold level positions in regard to gradient positions, and on-gradient raw image noise in comparison with in-media noise.

In the simplest case, if an image histogram includes two "separable" Gaussians, the mean values of the Gaussians may be determined with acceptable accuracy, and a threshold limit may be set to an average mean value. Setting the threshold limit to the average mean value may be enough to create acceptable binarization. However, in more difficult cases, choosing a proper threshold may not be that simple, and thresholding itself may be insufficient. What would still remain is statistically stable gradients on the substance's edges. One or more embodiments aim to estimate gradients behavior near the binarized substance edges. Several definitions are given below.

Raw Data

In the example shown on FIGS. 1-14, comparison of two 3-phase segmentations of the same image is provided. Herein, raw image data R is termed "initial image". Generally, R is an n-dimensional array. For example, raw image data R may be a tomographic 3D image or a 2D image from a scanning electron microscope. FIG. 1 shows an example of a 2D slice of a tomographic 3D image of sandstone.

$$G_R = \nabla R \tag{1}$$

Gradient Map $G_R$ is a "gradient map" of raw data grayscale values R. Inside the substance media $G_R$ is statistically equal to zero, on the edges, and for a given $\vec{x}$ near the substance surface, $G_R(\vec{x})$ is a vector with a direction orthogonal to this surface pointing into the substance (given that the substance is brighter than its surrounding).

Substance Mask

Figure 2A:
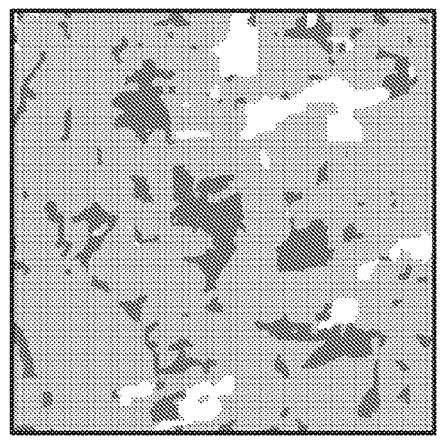
FIGS. 2A and 2B are images of segmentation substances masked by approaches described herein.
Figure 2B:
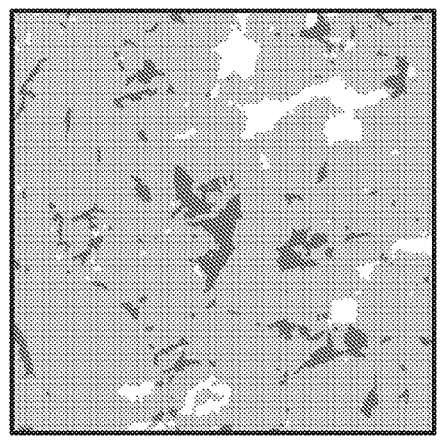
Figure 3A:
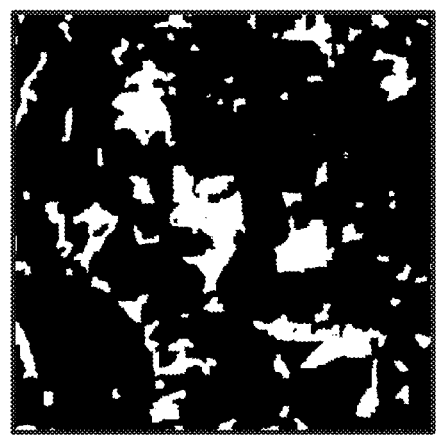
FIGS. 3A and 3B are binary masks for a first substance from the respective segmentation approaches of FIGS. 2A and 2B.
Figure 3B:
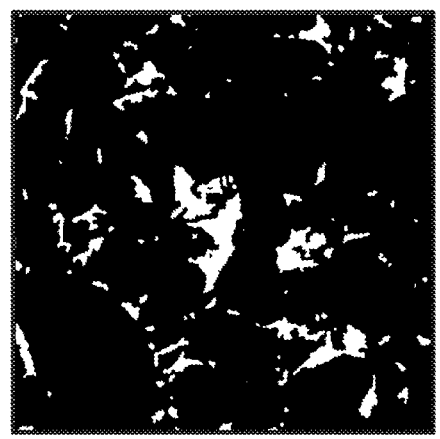
Figure 4A:
FIGS. 4A and 4B are binary masks for a second substance from the respective segmentation approaches of FIGS. 2A and 2B.
Figure 4B:
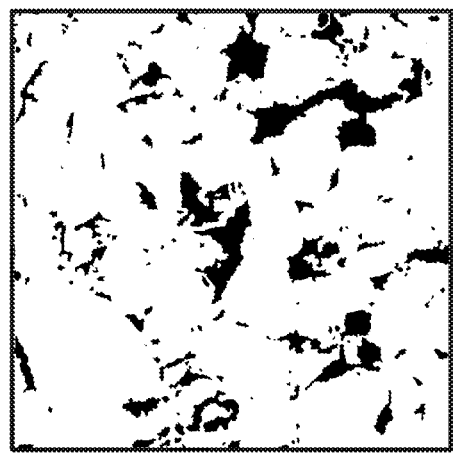
Figure 5A:
FIGS. 5A and 5B are binary masks for all substances not included as the first substance or the second substance from the respective segmentation approaches of FIGS. 2A and 2B.
Figure 5B:

A substance mask S, which may be a binarization mask B assumed to be a Boolean array with the same size as R, may be applied as input data. This is the segmentation the quality of which will be estimated. FIGS. 2A and 2B illustrate two slightly different segmentations, the quality of which will be compared. S values are substance indices ($s_1$=value (color) of first substance, $s_2$=value (color) of second substance, and so on). In FIGS. 2A and 2B $s_1$ is the darkest, $s_2$ is intermediate, and $s_3$ is the lightest. All the following steps of the disclosed quality control (QC) algorithm are carried out for all possible pairs of substances (changing sorting order inside pairs leads to trivial changes in results, so $\{s_1, s_2\}$ and $\{s_2, s_1\}$ are considered to be the same pair). This allows for an independent check of the correctness of edge position between two specific substances. After a pair $\{s_k, s_l\}$ is selected, three binary masks for this pair are defined as follows: $B_1=(S==s_k)$, $B_2=(S==s_1)$, $B_3=\sim(B_1|B_2)$. Here "~" stands for logical "NOT", and "|" stands for logical "OR". In the present example, $\{s_1, s_2\}$ is the selected pair, for which the following binary masks (shown in FIGS. 3A, 3B, 4A, 4B, and 5A, 5B) are created: $B_1$ (FIGS. 3A, 3B) corresponds to the darkest areas on FIG. 1, $B_2$ (FIGS. 4A, 4B) corresponds to the intermediate color areas on FIG. 1, and $B_3$ (FIGS. 5A, 5B), which is NOT substance 1 OR substance 2, therefore corresponds to substance 3 (white areas), since there are only three substances in this case.

Distance Mask

Distance mask D is an array of the same size as the raw image R. This mask provides the measure of the shortest distance from each voxel to the nearest edge of the substance under consideration. It may be determined in various ways (e.g., Euclidian distance).

Figure 6A:
FIGS. 6A and 6B are distance masks for the first substance of FIGS. 3A and 3B from the respective segmentation approaches of FIGS. 2A and 2B.
Figure 6B:

In accordance with one or more embodiments, D is Gaussian-blurred B (examples for substance 1 ($D_1$) are shown in FIGS. 6A and 6B. $D_2$ and $D_3$ are defined similarly to $D_1$). In this case distance mask provides values from 0 to 255 (for 8-bit binarization mask B, where 255 corresponds to the concerned substance and 0 to all other voxels). These distance mask values should be interpreted as follows: 128—original substance border on B, 0—voxels far outside from the substance, 255—voxels located deep inside the substance). For different blurring kernel sizes, these values (grayscale range) represent different geometrical distances in near-edge space. In accordance with the described method, the quality check of segmentation is performed separately for each pair of substances. Such approach requires modification of the distance map defined above for excluding voxels that were affected by substances out of consideration. Analyzing segmentation quality of pair $\{s_1, s_2\}$ a binary mask is created, $B_g=(D_3==0)$. $B_g$ represents areas of substances 1 and 2 ($B_1|B_2$) that are located far from other substances ($B_3$), i.e. lying some distance from other substances.

Edge Profile

On the basis of the definitions above, an element of the described QC algorithm may be calculated. For each grayscale level gradient distributions are obtained using distance mask as a measure of distance from the edge between substances. In one or more embodiments, mean absolute value and its standard deviation are used for further analysis of such distributions. Dependence of mean absolute gradient value $G_{R_{abs}}$ on the distance from the edge between considered substances should be interpreted as absolute gradient value profile on the edges averaged over the whole image. Such Edge Profile is estimated as a one-dimensional (1D) function:

$$G_{R_{abs}}(i) = \langle |G_R(\vec{x})| \rangle ; \vec{x} : (D_1(\vec{x})==i) \text{ and } (B_g(\vec{x})) \tag{2}$$

for all possible i distance mask values (from 0 to 255 for the considered example). For each distance value i, the mean absolute value of all $G_R$ voxels is calculated, for which two conditions are satisfied:

$D_1$ values in these voxels are equal to i $B_g$ values in these voxels are TRUE, i.e. these voxels are far from substances different from substances 1 and 2.

(Here $\langle X \rangle$ stands for mean value, |X| for vector length).

The standard deviation of these values can be defined as follows (with the same conditions on $\vec{x}$ selection):

$$\sigma_{G_{R_{abs}}}(i) = \sqrt{\langle |G_R(\vec{x})|^2 \rangle - \langle |G_R(\vec{x})| \rangle^2} ; \tag{3}$$

$\vec{x} : (D_1(\vec{x}) == i)$ and $(B_g(\vec{x}))$

Properties of Edge Profile

Examples of $$G_{R_{abs}}(i)$$

(71 and 72) and standard deviation $$\sigma_{G_{R_{abs}}}(i)$$

Figures 7A, 8A:
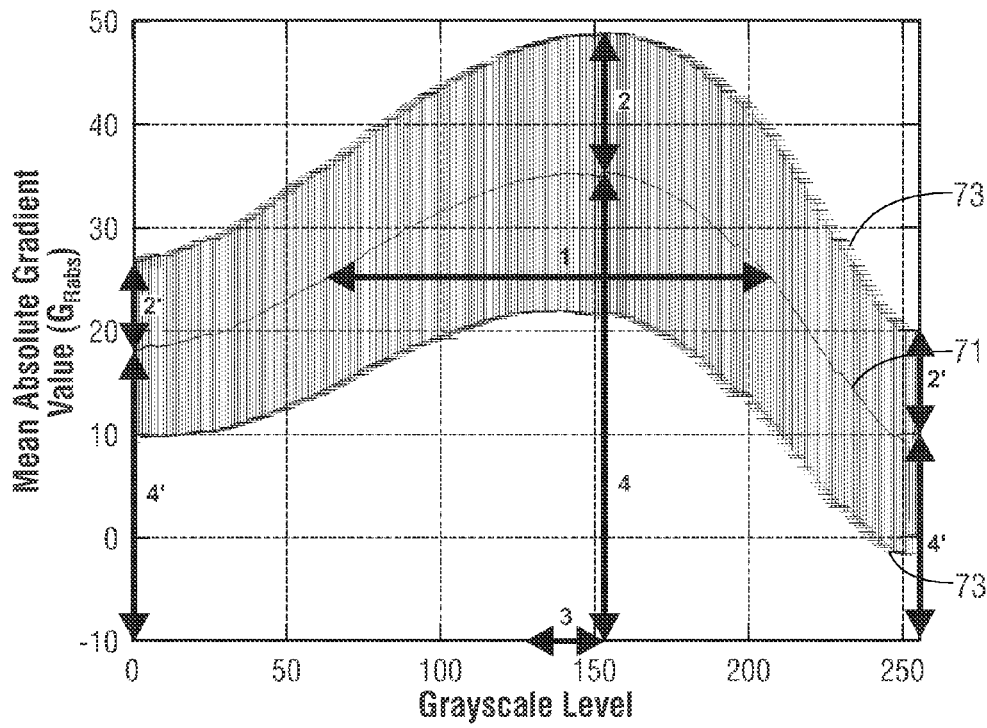
FIG. 7A shows the Edge Profile, as defined herein, between the first substance (see FIG. 3A) and the second substance (see FIG. 4A) from segmentation according to the segmentation approach of FIG. 2A.
FIGS. 8A and 8B are the results of analysis of FIGS. 7A and 7B, respectively.
Figures 7B, 8B:
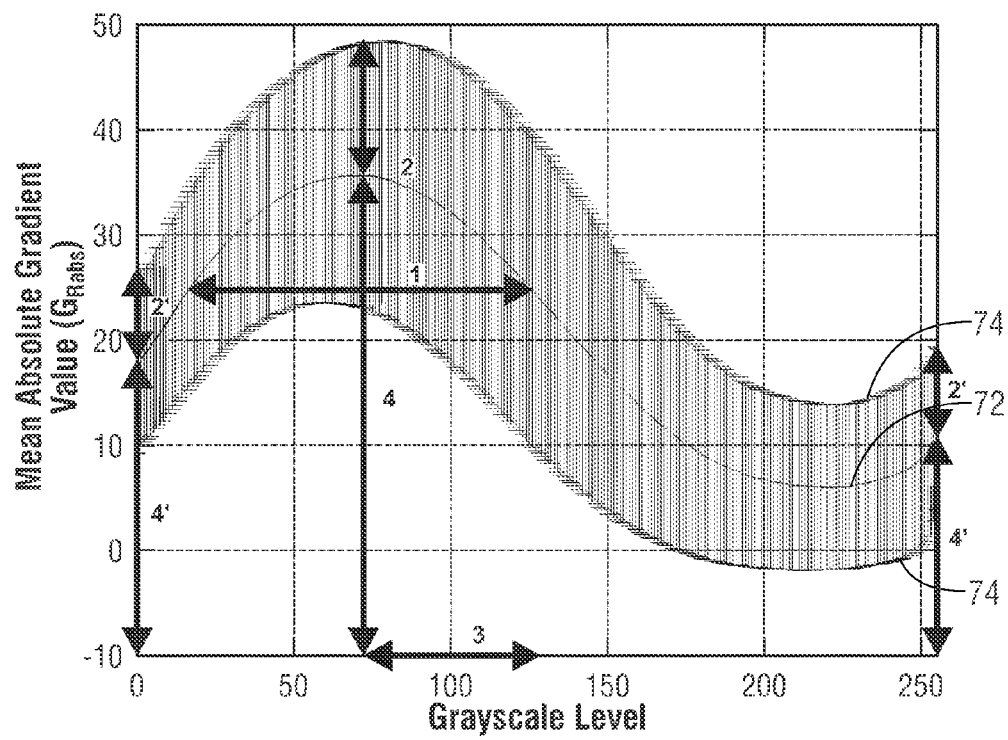
FIG. 7B shows the Edge Profile, as defined herein, between the first substance (see FIG. 3B) and the second substance (see FIG. 4B) from segmentation according to the segmentation approach of FIG. 2B.

(73 and 74) are presented in FIGS. 7A and 7B. Analysis of segmentation between substance 1 and substance 2 is accompanied by FIGS. 8A and 8B. In one or more embodiments, further statistical analysis of $$G_{R_{abs}}(i)$$

and $$\sigma_{G_{R_{abs}}}(i)$$

may be performed using the following values:
1. Full width at the half-height (FWHH) $Q_{FWHH}$ of the peak; (arrows labeled 1 on FIGS. 7A and 7B).
2. Ratio $$Q_{sigmacontrast} = \sigma_{G_{R_{abs}}}(i_{peak})/\langle \sigma_{G_{R_{abs}}}(0), \sigma_{G_{R_{abs}}}(255)\rangle^*;$$

(arrows labeled 2 at the peak and 2' at grayscale levels 0 and 255 on FIGS. 7A and 7B).
3. Peak shift $i_{peak}^{shift}$, the grayscale shift of the peak from the center of the grayscale range; (arrows labeled 3 on FIGS. 7A and 7B).
4. Peak contrast $Q_{peakcontrast} = G_{R_{abs}}(i_{peak})/\langle G_{R_{abs}}(0), G_{R_{abs}}(255)\rangle^*$; (arrows labeled 4 at the peak and 4' at grayscale levels 0 and 255 on FIGS. 7A and 7B).

\* 255 is the value for 8-bit case.

Full width at the half-height $Q_{FWHH}$ is calculated as follows:

$$G_{HH} = \langle G_{R_{abs}}(0), 2G_{R_{abs}}(i_{peak}), G_{R_{abs}}(255)\rangle,$$

$$i_1 = \max[\{i: G_{R_{abs}}(i-1) < G_{HH}\} \cap \{i < i_{peak}\}],$$

$$i_2 = \min[\{i: G_{R_{abs}}(i+1) < G_{HH}\} \cap \{i > i_{peak}\}],$$

$$Q_{FWHH} = i_2 - i_1 \quad (4)$$

where $G_{HH}$ is the absolute gradient value corresponding to half-height, and $i_1$ and $i_2$ are left and right grayscale values corresponding to FWHH.

From the above values, the following interpretation may be applied.
1. $Q_{FWHH}$ mainly depends on two factors:
    Image sharpness. Smaller $Q_{FWHH}$ means a sharper raw image. Generally, sharper images are easier to segment.
    Simpler substance border. The simpler the substance border morphology (e.g., mineral grains shape) the lower $Q_{FWHH}$ value that results. The simplest shape is a circle or sphere. An example of a complicated shape is a star, since a star has many narrow features. Simple shapes are usually easier to segment as well (e.g., glass beads sample).
Thus, $Q_{FWHH}$ may be considered in two ways:
    When comparing two different initial images processed by the same segmentation method, generally, lower $Q_{FWHH}$ values indicate lower risk of incorrect segmentation.
    When comparing two different segmentations of the same initial image, $Q_{FWHH}$ will be lower for segmentation accurately following all border features of considered substances. Thus, segmented borders will be more complex. Larger $Q_{FWHH}$ corresponds to more simplified edges of substances.
2. $Q_{sigmacontrast}$ may be considered as an indirect measure of border positioning adequacy over the entire image in contrast to direct average parameter $i_{peak}$. Standard deviation values $$\sigma_{G_{R_{abs}}}(0)$$

and $$\sigma_{G_{R_{abs}}}(255)$$

correspond to voxels far from the edge between considered substances. They mainly depend on image noise. In contrast, $$\sigma_{G_{R_{abs}}}(i_{peak})$$

is produced by image noise and improper position of the analyzed edge across the whole image. Thus, the larger the value of $Q_{sigmacontrast}$ the greater the range of possible errors in edge locations. Generally, $Q_{sigmacontrast}$ should not be much greater than 1.
3. $i_{peak}^{shift}$ is responsible for segmented edge shifting from the middle of the transitional area between substances on the image. This middle position (model ideal case for edge positioning) is 128 for 8-bit grayscale images. The smaller the absolute value of $|i_{peak}^{shift}|$, the closer to ideal the segmentation.
4. $Q_{peakcontrast}$ relates to the strength of the gradient on the edges between analyzed substances.
    When comparing two different initial images processed by the same segmentation method, peak contrast is an evidence measure of edge existence between substances. Generally, it is easier to segment an image if the gradient on the edge is strong enough and the transition is more evident. Thus, high $Q_{peakcontrast}$ indicates lower risk of incorrect segmentation.
    When comparing two different segmentations of the same initial image, lower peak contrast corresponds to lower quality of segmentation.

In FIGS. 8A and 8B the results of analysis for the considered example are presented. Based on the analysis results, a conclusion may be made that the threshold level between substance 1 and substance 2 is lower for segmentation approach 2 ($i_{peak} < 128$) and slightly higher for segmentation approach 1 ($i_{peak} > 128$). Segmentation approach 1 for substance 1 and substance 2 has visually better quality (as shown in FIG. 2A) corresponding to smaller $Q_{FWHH}$ (arrow 3 shown in FIG. 7A).

Other Approaches

Figure 9A:
FIGS. 9A, 9B, and 9C are sandstone pore geometries at micro-computed tomography (micro-CT) voxel size resolutions of 0.7 µm, 1.5 µm, and 3.0 µm, respectively.
Figure 9B:
Figure 9C:

Another digital rock model segmentation quality control tool is multi-scale imaging by a variety of techniques. Micro-CT scanning at different resolutions allows a reduction in the number of artifacts, as shown in FIGS. 9A-9C, where the result of decreasing resolution is the disappearance of a solid part of the rock. Constructing an adequate digital rock model that represents geometry is important to optimize resolution. The example shown in FIGS. 9A-9C shows changing of sandstone pore geometry at different micro-CT voxel size resolutions of 0.7 μm, 1.5 μm, and 3.0 μm, respectively.

Figure 10:
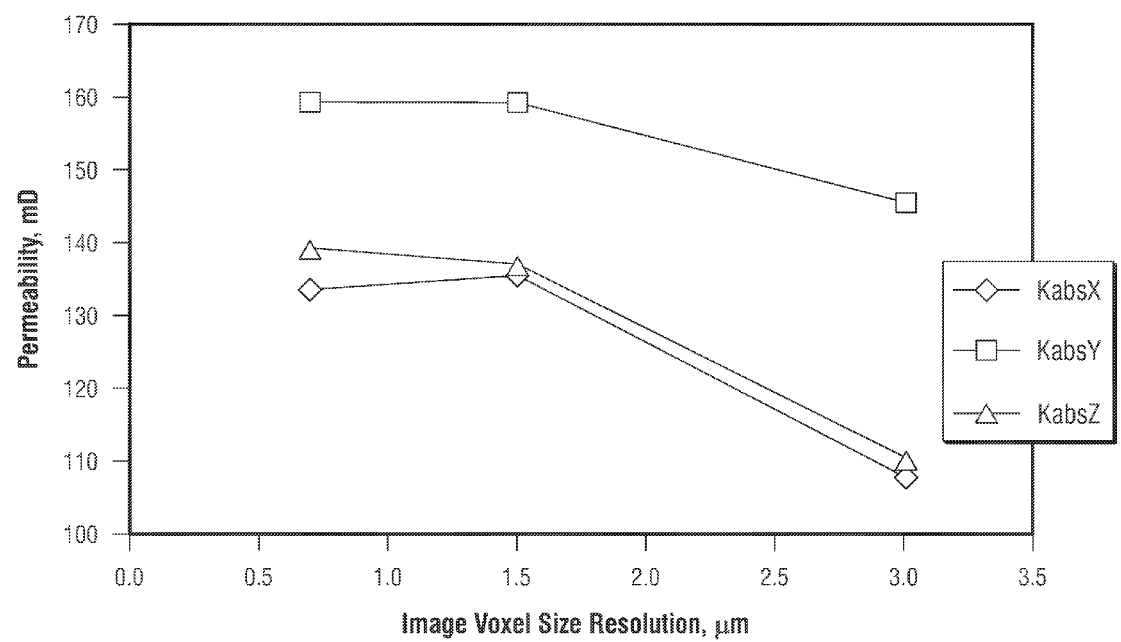
FIG. 10 illustrates the effect of image voxel size resolution on the results of simulation of permeability.

Geometry changes, such as those that result from changes in resolution, influence simulated petrophysical properties. FIG. 10 illustrates an example showing the variation in air permeability in the x, y and z directions for digital rock models having different geometries because they were acquired from the same physical sample at different resolutions.

An additional digital rock model segmentation quality control uses digital core analysis simulations in comparison with physical laboratory measurements. Performing one or more laboratory test measurements on the same or a similar rock or other porous medium is used to obtain one or more physical properties of the material. The laboratory test measurements may include but are not limited to the following: Routine Core Analysis, Special Core Analysis, electrical resistivity, geomechanical properties, and sample porosity.

Digital core analysis simulation is performed for at least one experimentally measured physical property using the digital model of the same or similar rock or other porous medium. The simulated properties may include but are not limited to the following: Routine Core Analysis, Special Core Analysis, electrical resistivity, geomechanical properties, and sample porosity. In one of the embodiments, the digital core simulations can reproduce laboratory conditions and experimental setup of the laboratory test.

One or more comparisons between laboratory test measurements and digital core simulations may be carried out. Comparison data may be used for a quality check of digital model construction. The comparison may be based on any form of mathematical or statistical analysis and uses an estimation of relative difference between experimental measurement and modeling.

The quality control approaches allow optimizing segmentation to create an adequate digital rock model. Physical laboratory measurements of rock properties are used to make complex digital rock models and play the role of an additional digital rock model quality check.

Figure 11A:
FIGS. 11A, 11B, and 11C are, respectively, a raw grayscale image of a carbonate sample, a segmented image of the carbonate sample using a segmentation quality control (QC) check, and microporosity mapping of the carbonate sample by calibrated grayscale level.
Figure 11B:
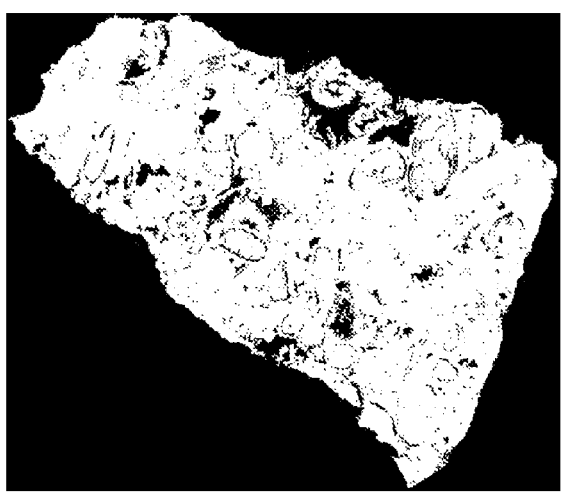
Figure 11C:
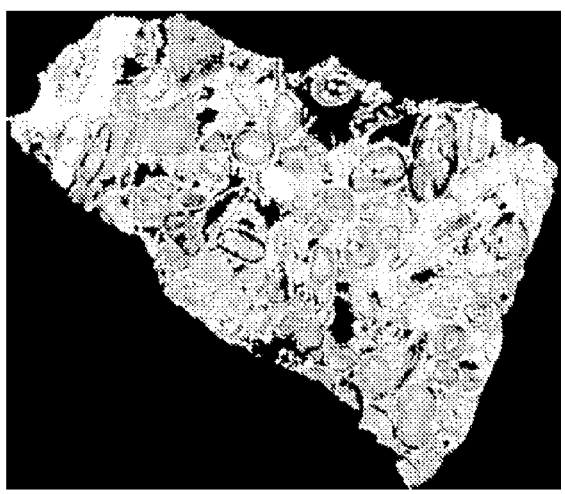

An example in FIGS. 11A-11C illustrates a workflow for microporosity mapping of a carbonate sample. A raw grayscale image (FIG. 11A) represents X-ray attenuation distribution within the core sample. An X-ray tomography method provides a means for reconstruction of the spatial distribution of linear attenuation coefficient (LAC) of X-rays within the rock sample.

The value of the LAC ($\mu$) of every phase depends on its chemical composition, material density, and X-ray radiation energy as presented in the equation below:

$$\mu = \mu_m \rho \qquad (5)$$

where $\mu_m$ is mass attenuation coefficient that depends on X-ray radiation energy and chemical composition of the material ($cm^2/g$); and $\rho$ is material density ($g/cm^3$).

The equation provides a means for correlating the local LAC values represented by grayscale levels in 3D images with density.

Volumetric Microporosity Mapping

The grayscale image of FIG. 11A may be used as input data for segmentation with a QC check (shown in FIG. 11B). Microporosity mapping by calibrated grayscale level—using digital model porosity, X-ray attenuation values, and routine laboratory measurements of total rock porosity—is applied to create a complex digital rock model (shown in FIG. 11C).

Digital core images may be used to create a complex digital rock model with mapping of microporosity, electrical conductivity, wettability and other rock properties. This complex digital rock model can be input data for digital core analysis simulation of rock properties.

The microporosity mapping workflow may have three main input datasets: binary image with quality control, calculated X-ray attenuation coefficients for the image (from micro-CT image), and porosity measurements for the same rock volume in a laboratory. Micro-CT resolution may not be sufficient to resolve or define all porous structures. Thus, porosity of binary digital rock model (representation of rock geometry) may be less than what is measured in the laboratory. That is why the X-ray attenuation coefficient is used, which is sensitive to material density change (such as the presence of micro-pores which are below resolution). To determine the porosity in the micro-pores that are below resolution, the value of porosity from a physical laboratory measurement minus the porosity of the digital rock model is used. The final step is construction of a complex digital rock model, which is again a 2D or 3D grayscale image, but now each value of the grayscale level means a particular value of microporosity.

Electrical conductivity, for example, depends on the value of microporosity. Thus, based on the value of microporosity, a particular value of conductivity can be defined for different parts of the digital rock model (grayscale image). Wettability can be defined by saturating a laboratory sample with different fluids (brine/oil/surfactants) and then imaging the fluids in the sample to distinguish their distribution. Then a preferred value of wettability may be assigned to a particular part of the rock surface (represented as voxels in the digital rock model).

One or more embodiments is a workflow that incorporates image processing for digital rock model construction and a segmentation quality control (QC) check based on a statistical approach followed by creation of a complex model tuned by laboratory test results. Image analysis and laboratory test results may be used to define a digital model for adequate representation of rock geometry and characteristic structural properties. The refinement improves understanding of the physical nature of the rocks. Lab tests that may be performed may include whole core, micro-, or nano-CT, scanning electron microscopy, focused ion beam scanning electron microscopy, confocal imaging, laser scanning fluorescence microscopy and other laboratory imaging techniques that can provide 2D or 3D images, and laboratory test measurements on the same or a similar rock or other porous medium to obtain one or more physical properties of the material, for example porosity and air permeability, and any additional laboratory testing of rock properties used to assign specific surface or bulk properties to a digital rock model.

Figure 12A:
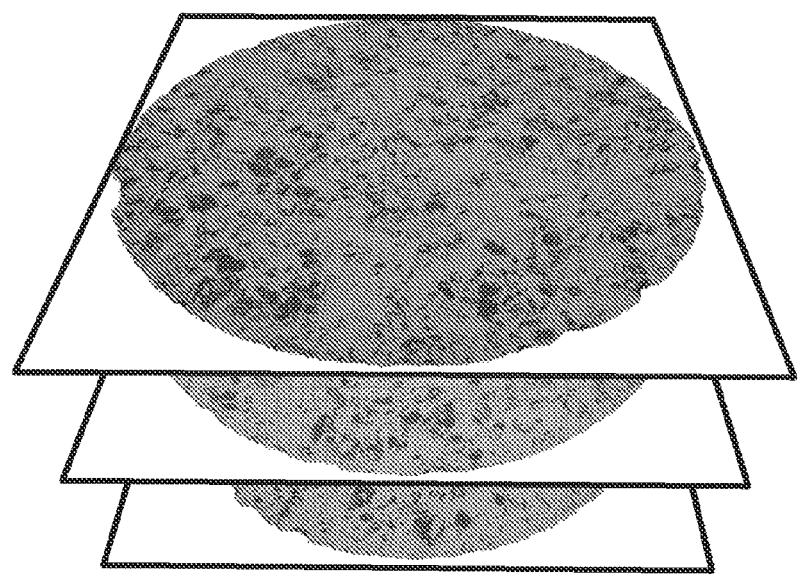
FIG. 12A illustrates a stack of 2D grayscale images of a digital core image.
Figure 12B:
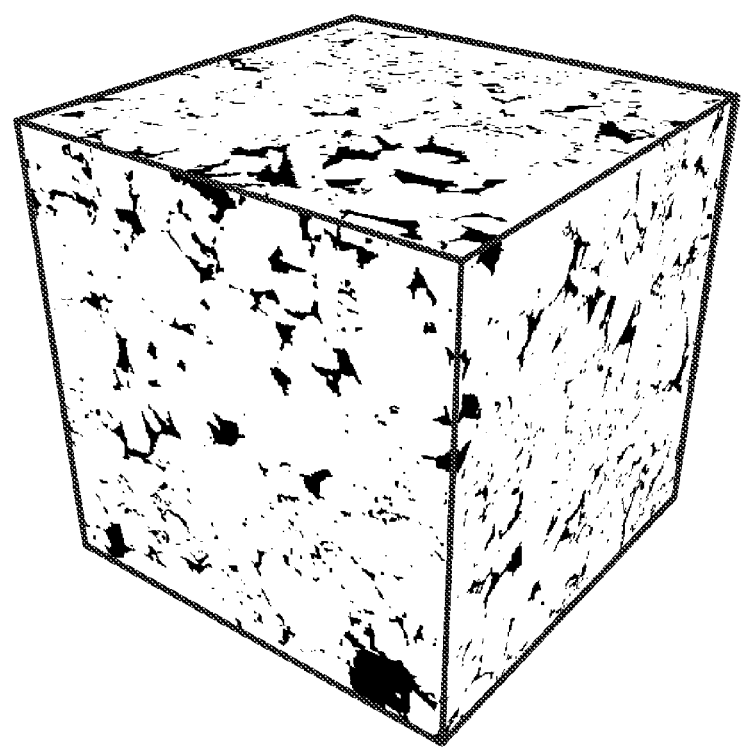
FIG. 12B illustrates an example of the segmentation of the digital core image of FIG. 12A.
Figure 13:
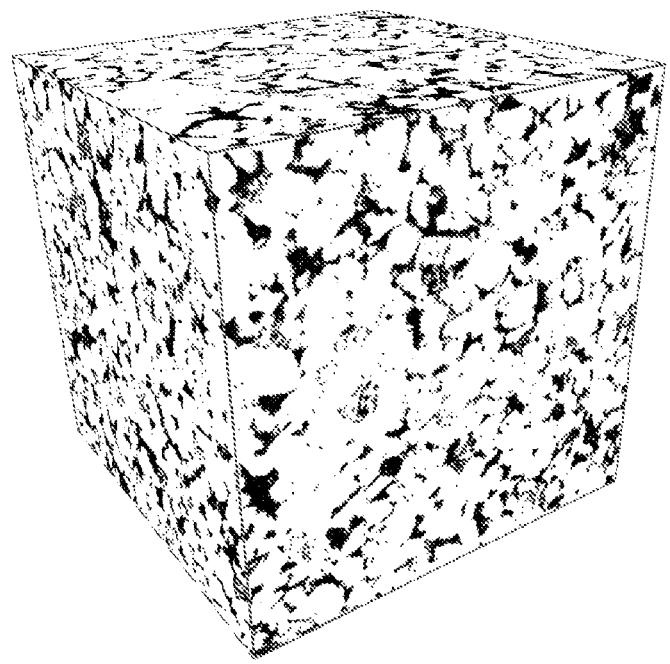
FIG. 13 illustrates a complex digital core model generated from the digital core image of FIG. 12A and the segmented image of FIG. 12B.

Complex digital core model construction may include (i) performing rock imaging, such as an individual or stack of 2D grayscale slices or 3D image; (ii) performing segmentation with a quality control check, where the segmented image may be, for example, a 2D or 3D binary image of surface or volume or an initial whole size grayscale image; and (iii) creating a complex digital model, such as a 2D or 3D image with grayscale calibrated to microporosity, flow properties, mechanical properties, or chemical reactivity, or a combination of these properties. FIG. 12A shows a stack of 2D grayscale images (i.e., the digital core image in the example). FIG. 12B shows an example of the segmentation of the digital core image in FIG. 12A. FIG. 13 shows a complex digital core model generated from the digital core image and the segmented image from FIGS. 12A and 12B.

Figure 14:
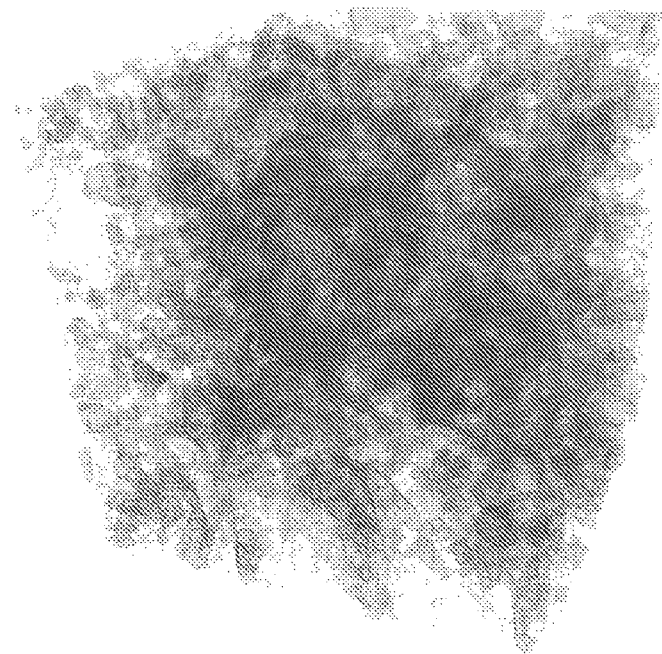
FIG. 14 illustrates a fluid flow model derived from digital core analysis simulation using the digital core model of FIG. 13.

In FIG. 13 black represents fully void spaces, white represents fully solid spaces, and blue to red represents voxels with microporosity from 0% to 100%, respectively. The complex digital core model may be further used for digital core analysis simulations such as fluid flow modeling shown in FIG. 14. In FIG. 14 red represents oil-saturated void spaces, blue represents water-saturated void spaces, and the solid minerals are transparent.

One or more disclosed embodiments may perform one or more of the following. Porous material imaging may be performed using X-ray computed tomography, scanning electron microscopy, focused ion beam scanning electron microscopy, confocal microscopy, laser scanning fluorescence microscopy or other means that result in either a 2D or a 3D digital representation of that material. A 2D or 3D digital model of a sample of a rock or other porous material is made based on segmentation with quality control by image processing and analysis, multi-scale imaging, and properties simulation. One or more image segmentations are performed to make one or more quality checks. These segmentations may include but are not limited to the following: global or local thresholding, or based on other approaches such as indicator kriging as described in *Image Thresholding by Indicator Kriging*, Wonho Oh and W. Brent Lindquist, *IEEE Transactions on Pattern Analysis & Machine Intelligence,* 1999 Volume 21, Issue No. 07—July, pp 590-602.

Further, one or more multi-scale imaging methods may be performed on the same or a similar rock or other porous medium to resolve structural features in different regions. The imaging methods may include but are not limited to the following: X-ray whole core, micro-, or nano-computed tomography, focused ion beam scanning electron microscopy, confocal microscopy, and laser scanning fluorescence microscopy.

One or more embodiments of the invention may perform one or more additional laboratory test measurements on the same or a similar rock or other porous medium, provided that the sample size is bigger or smaller than the one used for the first laboratory test. At least one comparison between at least one physical property experimentally measured on the sample of different size may be performed. The comparison data may be used for the estimation of relative difference between two sets of experimental data.

A complex digital rock model is constructed using the calibrated grayscale which includes but is not limited to the following rock properties: microporosity, electrical conductivity, wettability, chemical reactivity, thermal conductivity, elastic, and adsorption.

Although only a few example embodiments have been described in detail above, those skilled in the art will readily appreciate that many modifications are possible in the example embodiments without materially departing from the invention. Accordingly, all such modifications are intended to be included within the scope of this disclosure as defined in the following claims.

What is claimed is:

1. A method for analysis comprising:
    obtaining a digital core image from a subterranean sample of a geological formation, wherein the digital core image comprises a plurality of voxel values, each representing a physical property of the geological formation;
    performing a plurality of segmentations on the digital core image using a plurality of approaches to obtain a plurality of segmented images, wherein at least one of the plurality approaches is based on a threshold of the voxel values;
    performing a statistical analysis on the plurality of segmented images to select the most suitable approach of the plurality of approaches; and
    generating a digital core model using a segmented image of the plurality of segmented images.

2. The method of claim 1, further comprising performing a simulation test on the digital core model to obtain a model test result.

3. The method of claim 2, further comprising performing a field operation based on the model test result.

4. The method of claim 3, wherein the field operation comprises a survey operation.

5. The method of claim 3, wherein the field operation comprises a wellbore operation.

6. The method of claim 2, further comprising:
    performing a test on the sample to obtain a sample test result, wherein the sample test matches the simulation test;
    determining that the sample test result does not match the model test result; and
    updating the segmented image based on the model test result and determining that the sample test result matches the model test result.

7. The method of claim 1, further comprising:
    selecting the physical property of the subterranean sample for analysis;
    identifying a plurality of gradients of a substance in the digital core image;
    for each portion of the substance in the digital core image, identifying the physical property in the portion based on a gradient of the portion to obtain an identified physical property; and
    updating the digital core model based on the identified physical property in each portion.

8. A system for analysis comprising:
    a computer processor,
    a data repository configured to store a digital core image of a subterranean sample of a geological formation and a digital core model, wherein the digital core image comprises a plurality of voxel values, each representing a physical property of the geological formation, and
    a digital core modeling tool comprising instructions, when executed, causing the computer processor to:
        perform a plurality of segmentations on the digital core image using a plurality of approaches to obtain a plurality of segmented images wherein at least one of the plurality approaches is based on a threshold of the voxel values,
        perform a statistical analysis on the plurality of approaches using the plurality of segmented images to select an approach of the plurality of approaches, and
        generate the digital core model using a segmented image of the plurality of segmented images,
        wherein the segmented image corresponds to the most suitable approach.

9. The system of claim 8, further comprising a simulation tool configured to perform a simulation test on the digital core model to obtain a model test result.

10. The system of claim 8, further comprising a display configured to display the digital core model.

11. A system comprising:
a surface unit comprising a computer processor and a controller, wherein the controller is configured to actuate mechanisms in a field to perform field operations; and
a digital core modeling system operatively coupled to the surface unit, said digital core modeling system comprising instructions, when executed, causing the computer processor to:
   perform a plurality of segmentations on a digital core image, of a subterranean sample of a geological formation, using a plurality to approached to obtain a plurality of segmented images, wherein the digital core image comprises a plurality of voxel values, each representing a physical property of the geological formation,
   perform a statistical analysis on the plurality of approaches using the plurality of segmented images to select an approach of the plurality of approaches wherein at least one of the plurality approaches is based on a threshold of the voxel values, and
   generate a digital core model using a segmented image of the plurality of segmented images, wherein the segmented image corresponds to the approach,
   wherein said digital core model is provided to the surface unit.

12. The system of claim 11, wherein the controller is configured to actuate the mechanisms based on the digital core model.

* * * * *